(12) United States Patent
Flint

(10) Patent No.: US 8,706,207 B2
(45) Date of Patent: Apr. 22, 2014

(54) METHOD AND APPARATUS FOR MEASURING AND TREATING SHIVERING DURING THERAPEUTIC TEMPERATURE CONTROL

(75) Inventor: Alexander C Flint, Menlo Park, CA (US)

(73) Assignee: Bedrock Inventions, LLC, Menlo Park, CA (US)

( * ) Notice: Subject to any disclaimer, the term of this patent is extended or adjusted under 35 U.S.C. 154(b) by 893 days.

(21) Appl. No.: 12/575,708

(22) Filed: Oct. 8, 2009

(65) Prior Publication Data

US 2010/0087900 A1  Apr. 8, 2010

Related U.S. Application Data

(60) Provisional application No. 61/103,815, filed on Oct. 8, 2008, provisional application No. 61/176,015, filed on May 6, 2009.

(51) Int. Cl.
*A61B 5/04* (2006.01)
*A61B 5/0402* (2006.01)
*A61B 5/0408* (2006.01)
*A61B 5/0488* (2006.01)

(52) U.S. Cl.
USPC .......... 600/546; 600/300; 600/301; 600/547; 600/595

(58) Field of Classification Search
USPC .......... 600/300, 301, 546, 547, 595; 607/104, 607/105, 113
See application file for complete search history.

(56) References Cited

U.S. PATENT DOCUMENTS

| 6,141,572 | A | 10/2000 | Haas |
| 6,149,670 | A | 11/2000 | Worthen et al. |
| 6,188,930 | B1 | 2/2001 | Carson |
| 6,197,045 | B1 | 3/2001 | Carson |
| 6,231,594 | B1 | 5/2001 | Dae |
| 6,290,717 | B1 | 9/2001 | Philips |
| 6,375,674 | B1 | 4/2002 | Carson |
| 6,432,124 | B1 | 8/2002 | Worthen et al. |
| 6,454,793 | B1 | 9/2002 | Evans et al. |
| 6,461,379 | B1 | 10/2002 | Carson et al. |

(Continued)

FOREIGN PATENT DOCUMENTS

| JP | 2002191579 A | * | 7/2002 | ............... A61B 5/11 |
| JP | 2002-224069 A | | 8/2002 | |

(Continued)

OTHER PUBLICATIONS

International Search Report and Written Opinion, mailed May 13, 2010, International application No. PCT/US2009/060029.

(Continued)

*Primary Examiner* — Sean Dougherty
(74) *Attorney, Agent, or Firm* — Bill Kennedy Patents; Bill Kennedy

(57) ABSTRACT

Methods and apparatus for the prevention and treatment of shivering encountered during therapeutic temperature regulation are disclosed that utilize an active system of counter-warming such that the timing and intensity of warmth provided to selected body areas is regulated dynamically in response to such factors as the extent of cooling applied to the core, the degree of shivering encountered, and patient temperature. Additionally, methods and apparatus are disclosed for the measurement and quantification of shivering for use in this and other applications.

40 Claims, 14 Drawing Sheets

(56) References Cited

U.S. PATENT DOCUMENTS

| | | |
|---|---|---|
| 6,582,457 B2 | 6/2003 | Dae et al. |
| 6,620,187 B2 | 9/2003 | Carson et al. |
| 6,645,232 B2 | 11/2003 | Carson |
| 6,648,905 B2 | 11/2003 | Hoglund et al. |
| 6,660,027 B2 | 12/2003 | Gruszecki et al. |
| 6,669,715 B2 | 12/2003 | Hoglund et al. |
| 6,682,551 B1 | 1/2004 | Worthen et al. |
| 6,692,518 B2 | 2/2004 | Carson |
| 6,702,839 B1 | 3/2004 | Dae et al. |
| 6,726,710 B2 | 4/2004 | Worthen et al. |
| 6,799,063 B2 | 9/2004 | Carson |
| 6,802,855 B2 | 10/2004 | Ellingboe et al. |
| 6,818,012 B2 | 11/2004 | Ellingboe |
| 6,827,728 B2 | 12/2004 | Ellingboe et al. |
| 7,008,444 B2 | 3/2006 | Dae et al. |
| 7,294,112 B1 | 11/2007 | Dunlop et al. |
| 7,361,186 B2* | 4/2008 | Voorhees et al. ............. 607/104 |
| 7,811,992 B2* | 10/2010 | Skinner et al. ............... 514/16.4 |
| 8,032,224 B2* | 10/2011 | Miesel et al. .................. 607/46 |
| 2002/0091308 A1 | 7/2002 | Kipshidze et al. |
| 2002/0111657 A1 | 8/2002 | Dae et al. |
| 2003/0228371 A1* | 12/2003 | Skinner et al. ............... 424/530 |
| 2004/0064169 A1 | 4/2004 | Briscoe et al. |
| 2004/0087606 A1* | 5/2004 | Voorhees et al. ............. 514/282 |
| 2004/0143170 A1 | 7/2004 | DuRousseau |
| 2005/0065583 A1* | 3/2005 | Voorhees et al. ............. 607/104 |
| 2006/0058589 A1* | 3/2006 | Nijsen ........................... 600/301 |
| 2007/0063850 A1 | 3/2007 | Devaul et al. |
| 2007/0129622 A1* | 6/2007 | Bourget et al. ................ 600/382 |
| 2007/0191918 A1 | 8/2007 | MacHold et al. |
| 2007/0255118 A1* | 11/2007 | Miesel et al. .................. 600/300 |
| 2008/0071150 A1* | 3/2008 | Miesel et al. .................. 600/301 |
| 2008/0071324 A1* | 3/2008 | Miesel et al. .................... 607/46 |
| 2009/0033333 A1* | 2/2009 | Gribova et al. ................ 324/439 |
| 2009/0069703 A1* | 3/2009 | Takla et al. .................... 600/509 |
| 2009/0131835 A1 | 5/2009 | Voorhees et al. |
| 2009/0149779 A1 | 6/2009 | Russo et al. |

FOREIGN PATENT DOCUMENTS

| | | | |
|---|---|---|---|
| WO | WO 9830165 A1 * | 7/1998 | ............. A61B 19/00 |
| WO | WO0110323 | 2/2001 | |
| WO | WO 03/037158 A2 | 5/2003 | |
| WO | WO 2004/041171 A2 | 5/2004 | |
| WO | WO2007/088547 | 8/2007 | |
| WO | WO2009/065138 A1 | 5/2009 | |

OTHER PUBLICATIONS

UK IPO Combined Search and Examination Report dated Jul. 1, 2013 in Application No. GB1309167.3.
UK IPO Search Report, Examination Report dated May 1, 2013 in Application No. GB1303843.5.
UK IPO Combined Search and Examination Report dated Jul. 1, 2013 in Application No: GB1309167.3.
UK IPO Search Report, Examination Report dated May 1, 2013 in Application No: GB1303843.5.

* cited by examiner

ALIGN n TRACINGS

RAW TRACING     MEAN OF n TRACINGS

MEAN OF n FFT SPECTRA

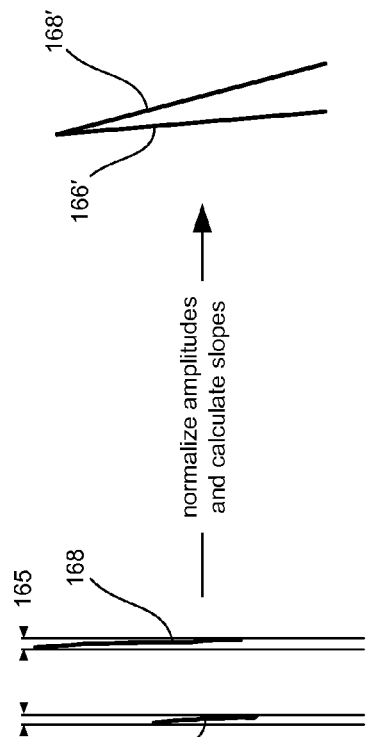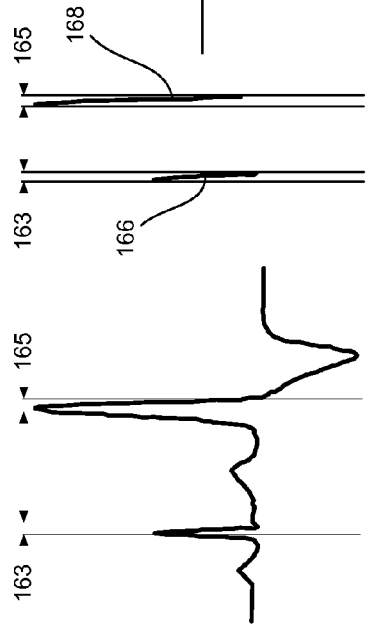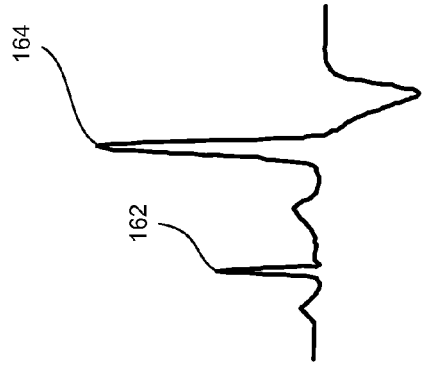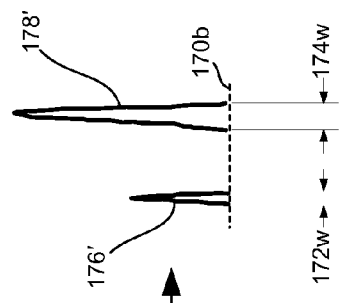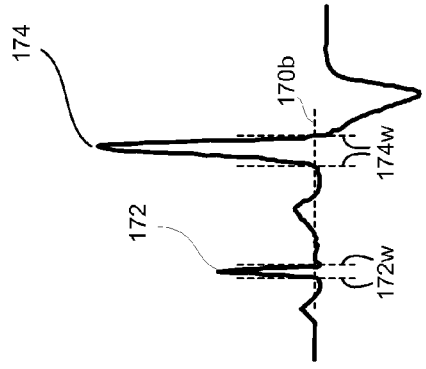

METHOD AND APPARATUS FOR MEASURING AND TREATING SHIVERING DURING THERAPEUTIC TEMPERATURE CONTROL

CROSS-REFERENCE TO RELATED APPLICATIONS

This application claims priority from Alexander Calhoun Flint U.S. Provisional Application No. 61/103,815, titled "Method and apparatus for active counterwarming and shivering quantification to treat and measure shivering during therapeutic temperature control", which was filed Oct. 8, 2008; and from Alexander C. Flint U.S. Provisional Application No. 61/176,015, titled "Method and apparatus for measuring and treating shivering during therapeutic temperature control", which was filed May 6, 2009. Each of the said applications is incorporated herein by reference.

BACKGROUND

1. Field of the Invention

This invention relates to therapeutic temperature regulation and, particularly, to controlling shivering during maintenance of normothermia or induced hypothermia.

2. Description of Related Art

Therapeutic induction of hypothermia and therapeutic maintenance of normothermia are used to protect at-risk brain tissue from secondary injury in the setting of anoxic brain injury after cardiac arrest and other central nervous system pathologies. A major limiting factor in the induction of hypothermia or maintenance of normothermia is the generation of shivering, which is a normal adaptive physiologic response that serves to bring the body temperature upwards. In addition, shivering in this context can have harmful physiological effects by diverting energy away from the critical organs such as the brain and heart.

Continuous counterwarming measures (("passive") counterwarming) have been found to have some degree of efficacy in treating shivering. When shivering is observed by attending medical personnel, an assessment is made by the personnel and, if judged to be indicated, a counterwarming therapy may be employed, for example by deploying a warming blanket onto or beneath the patient. Conventionally, passive counterwarming once applied is not adjusted over the therapeutic course.

Other anti-shivering measures in common use include pharmaceuticals; currently available options have limited efficacy and may have serious adverse effects, and the modes of administration may pose risks to the patient.

SUMMARY

In general the invention provides systems to quantify repetitive movements of a subject, and particularly to quantify shivering in a subject in the course of therapeutic temperature regulation and to apply counterwarming in a suitable regime for inhibition of shivering. The counterwarming regime can operate in a feedback system. In a therapeutic temperature regulation context, where core cooling is being applied to the patient for maintenance of normothermia or for induction of hypothermia, the system for shivering quantification and active counterwarming can be interfaced with the core cooling system. The counterwarming regime can be responsive to the quantified shivering, or to the core temperature of the patient, or to the amount of core cooling being applied, or to any combination of these factors.

In one general aspect the invention features a method for quantifying shivering in a subject, by obtaining a signal from a muscle mass that is susceptible to shivering; and quantifying shivering by analysis of the signal. In some embodiments obtaining the signal includes directly detecting movement using a periodic motion (vibration) detector such as an accelerometer; in some embodiments obtaining the signal includes obtaining an electrical signal from one or more electrodes, which may include an EMG signal or an ECG+EMG signal. In some embodiments obtaining the signal includes obtaining both directly detecting vibration of the muscle mass and detecting an electric signal from the muscle mass; in such embodiments the results of quantification of shivering from the two approaches can be combined. In some embodiments quantifying shivering includes performing a wave analysis such as a spectral density analysis on the signal; and quantifying shivering from the results of the spectral density analysis. In some such embodiments the spectral analysis yields a power spectrum. In some embodiments the wave analysis includes a Fourier analysis, such as for example a fast Fourier transform. In some embodiments the wave analysis includes an autocorrelation function followed by a Fourier analysis. At least some of the data and signal processing manipulations are carried out using a machine such as a microprocessor programmed to carry out the particular manipulations.

In some embodiments obtaining the signal includes detecting a combined ECG and EMG signal from the body surface overlying the muscle mass that is susceptible to shivering and processing the signal to remove the ECG component, resulting in the EMG signal component. In some such embodiments detecting the combined ECG+EMG signal includes applying any umber of electrodes at one or more sites on or in the skin overlying the muscle mass, or in the muscle mass itself. In other embodiments obtaining the signal includes detecting a combined ECG and EMG signal, digitizing the combined signal, and performing a wave analysis such as a spectral density analysis on the combined signal; in some embodiments the wave analysis is carried out on a frequency range of the spectrum that is known to correspond to a shivering EMG. In some embodiments the method further includes obtaining a signal prior to initiating a cooling treatment (a "baseline" signal), and processing the baseline signal by spectral analysis; then obtaining a signal during cooling (when shivering may be expected to occur), and processing the shivering signal by spectral analysis; then subtracting one signal from the other to obtain a spectrum that represents only the shivering component.

In some embodiments processing the combined signal includes digitizing the combined signal. In some embodiments the data separation is carried out on a set of traces, each of which may include a complete cardiac cycle. The EMG data can be separated from the combined ECG+EMG data by aligning the traces based on an easily identified feature of the ECG waveform such as the peak of the QRS complex of the ECG and signal averaging the digitized traces to isolate EMG-free ECG data, and subtracting the ECG data from the combined EMG and ECG data to yield ECG-free shivering EMG data. Where the data separation is carried out on a set of traces, the signals can be aligned and the separation can be carried out on selected segments of ECG tracings after alignment so that regions with minimal ECG data elements, such as for example the S-T segment and the region between the end of the T wave and the start of the P wave, are selectively analyzed. In some embodiments atypical ECG morphologies are detected, and cardiac cycles that include outliers are identified and removed from the analysis. In some embodiments atypical ECG morphologies are excluded from analysis by subtracting stored averaged ECG traces from the same patient under non-shivering conditions, with exclusion of traces that lead to significant residual ECG data (for example, residual voltage amplitude above an adjustable threshold or residual power spectral density in a frequency range lower or higher than that typically associated with shivering energy).

In some embodiments performing a wave analysis includes carrying out an averaged fast Fourier transform ("FFT") analysis. The averaged FFT analysis may be carried out by performing an FFT on each shivering EMG tracing followed by averaging the FFT spectra to yield an averaged FFT spectrum. In some embodiments, an autocorrelation function is performed on each shivering EMG trace to augment analysis of the rhythmic shivering activity, and then a Fourier analysis is performed on the results of the autocorrelation.

The intensity of shivering may be quantified by determining the amplitude of the peak spectral power (e.g., the peak Fourier spectrum power) within an appropriate frequency range that is typical for shivering EMG; or, the shivering may be quantified by determining the area under the curve of the spectral power within an appropriate frequency range that is typical for shivering EMG; or, the shivering may be quantified by analyzing appearances of different peaks corresponding to different frequencies of shivering that occur as shivering becomes more intense; or, the shivering may be quantified by analyzing change of spectral peaks or patterns as a function of time.

In some embodiments the measured shivering intensity may be used to generate a continuous scale or score variable as a function of time that represents shivering intensity. The resulting shivering intensity scale or score can be used as a means to influence other variables under control in temperature regulation; and/or, the shivering intensity scale or score can be displayed numerically or graphically for use by a clinician; and/or the shivering intensity scale can be transmitted to another device for use in another or an additional control process.

In another general aspect the invention features apparatus for quantifying shivering in a subject, by methods described above. The apparatus includes means for obtaining a signal from a muscle mass that is susceptible to shivering; and means for analyzing the signal. The means for obtaining a signal may include a direct motion detector, such as an accelerometer and leads from the detector to a signal processor; or an indirect motion detector, such as one or more electrodes adapted for placement in or on a surface of the body of the patient, and leads for electrical connection of the electrodes to a signal processor. Where the detector includes electrodes, the electrodes may include ECG electrodes or EMG electrodes, such as surface electrodes or needle electrodes. The means for analyzing the signal includes a signal processor adapted to receive signals from the means for obtaining the signal from the muscle mass, and configured to carry out any of the various data processing procedures outlined above, such as a microprocessor programmed to carry out the particular manipulations.

In another general aspect the invention features a method for applying active counterwarming to a patient, by quantifying shivering as outlined above, and regulating counterwarming dynamically in response to the quantified shivering or the patient's core temperature, or in response both to the quantified shivering or the patient's core temperature.

In another general aspect the invention features a method for applying active counterwarming to a patient during therapeutic temperature regulation of the patient. In some such embodiments the therapeutic temperature regulation includes cooling to reduce the core temperature. In some embodiments applying counterwarming includes applying warming to selected sites on the patient's body; the sites may be body areas not used for cooling the core, including for example hands, feet, or ears, or upper back, or posterior neck, or other sites, or a combination of these.

In some embodiments regulating the counterwarming includes adjusting the applied warming in relation to the intensity of shivering at a moment, or in relation to the patient's core temperature, or in relation to the intensity of core cooling, or in relation to any two or more of these. In some embodiments regulating the counterwarming includes adjusting the applied warming in relation to any of these or any combination of these, together with one or more of added constants, proportionality coefficients, or any mathematical manipulations or interactions of these variables.

In some embodiments regulating the counterwarming includes adjusting the applied warming in relation to the rate of any of or any combination of: change in cooling temperature per unit time, change in shivering intensity per unit time, or change in patient temperature per unit time; or any mathematical manipulations or interactions of these variables, such as for example a change in the square of any variable per unit time or the rate of change of any variable per unit time squared.

In some embodiments applying counterwarming includes any of: changing the temperature of warming applied to all treated body regions; changing the temperature of warming applied to specific treated body regions; changing the pattern of warming applied to selected treated body regions, for example by applying warming to different body regions at different times according to any number of patterns; applying warming in a successive fashion to sequential body regions, for example by warming the ears, then warming ears and hands, then warming the ears, hands and feet; applying selective warming to smaller regions, for example to fingers or toes; or applying warming to other body areas altogether; and warming various body regions in various patterns, including varying the intensity of warmth applied to different regions, and including thereby creating gradients of warmth.

In some embodiments regulating the counterwarming includes adjusting the applied warming in relation to any of one or more computer learning algorithms to determine over time the optimal means of shivering treatment in an individual patient.

In another general aspect the invention features apparatus for applying active counterwarming to a patient, including apparatus for quantifying shivering in a subject, as described above, and apparatus for warming selected areas of the patient's body.

In another general aspect the invention features apparatus for applying active counterwarming to a patient during therapeutic temperature regulation of the patient, including apparatus for quantifying shivering in a subject, as described above, and apparatus for warming selected areas of the patient's body; and further including apparatus for cooling the patient to lower the core temperature.

In some embodiments the apparatus for cooling the patient includes a temperature set point feedback device operatively connected to cooling apparatus; and a core temperature sensor operatively connected to the temperature set point feedback device. In some embodiments the cooling apparatus includes a cooling blanket, or cooling pads, or an endovascular cooling catheter.

In some embodiments the apparatus for warming selected areas of the body includes counterwarming elements, and a counterwarming controller operatively connected to the counterwarming elements and configured and adapted to adjust the warming applied to the counterwarming elements. In some embodiments the counterwarming controller is operatively connected to one or a combination of two or more of: a core temperature sensor; a core cooling controller; or the apparatus for quantifying shivering.

In some embodiments the counterwarming elements include heating apparel, including for example heated mittens, heated booties, heated ear muffs, or heated blankets above or below the body; the counterwarming elements can be heated by any of a variety of means for heat transfer; including in some embodiments circulating warm water (or other liquid), or insulated electrical heating coils. In some embodiments the counterwarming elements include apparatus configured for infusion of a suitable warm sterile liquid (for example, an aqueous or oil-based liquid) into the external auditory canals of both ears of the patient; such apparatus can include, for example, tubes (inflow and outflow) mounted through plastic earplugs.

Any of the various operative connections by which signals are sent and received by any of the various components in any of the embodiments may be wired or wireless. In particular treatment environments (for example, the intensive care unit) signal transfer by wireless transmitter and receiver pairs, using a wireless communications protocol such as "Bluetooth", may be preferred.

Further in general the invention provides systems for isolating a signal of interest from a combined signal containing superimposed first and second signals. The first signal is the signal of interest, and may have any of a variety of properties; the second signal includes recurring epochs or cycles of a stereotyped waveform, and may in addition have a relationship to an external event, such as an external trigger.

Accordingly, in one general aspect, the invention features isolation of a first signal from a combined ("A+B") signal containing first ("A") and second ("B") signals, wherein the second signal includes recurring epochs of a stereotyped waveform, by: digitally sampling the combined (A+B) signal at a suitable sample rate; storing a number (n) of epochs of the combined (A+B) signal; averaging the stored epochs of the combined signal to obtain an average of the (n) recurring epochs of the stereotyped waveform; and subtracting the average recurring epoch from each of at least a subset of the (n) epochs of the combined (A+B) signal and storing the results, containing isolated first (A) signal epochs substantially free of signal (B) features. At least some of the data and signal processing manipulations are carried out using a machine such as a microprocessor programmed to carry out the particular manipulations.

In some embodiments the initial sample of each combined (A+B) signal epoch is determined by identifying one or more characteristic features of B signal and using the identified feature to index the initial sample of each epoch. In some embodiments the B signal has a characteristic peak, and in such embodiments a thresholding technique can be used to identify the peak and to use a feature (e.g., the apex) of the peak as an initial sample of an epoch. In some embodiments the B signal has a temporal relationship to an external event, and an occurrence of the external event can be used to index the start of an epoch. In some embodiments each epoch begins at the indexed first sample and ends at the sample immediately preceding the first sample of the subsequent epoch (a "complete" epoch); in other embodiments the epochs may be truncated.

In averaging the stored combined (A+B) epochs, a sufficient number of epochs are averaged to provide an average signal B substantially free of signal A, that is, to reduce the contribution of signal A so that the average signal B is substantially uncontaminated by signal A components.

The stored isolated signal A epochs may thereafter be subjected to analysis, for example including performing a wave analysis such as a spectral density analysis on the signal. The spectral analysis may yield a power spectrum, for example. The wave analysis may for example include a Fourier analysis, such as for example a fast Fourier transform. The wave analysis may in some embodiments include an autocorrelation function followed by a Fourier analysis.

In embodiments where complete combined (A+B) signal epochs are stored, the isolated signal A epochs can be rejoined end-to-end to reconstruct an extended (reconstructed) signal A having a duration longer than the isolated signal A epochs.

Combined signals of any of a variety of types, from any of a variety of sources, may be treated in this manner.

BRIEF DESCRIPTION OF THE DRAWINGS

FIGS. 16A, 16B, 16C and 16D are graphical representations illustrating stages in a method for identifying outlier waveforms according to an embodiment of the invention.

FIGS. 17A, 17B and 17C are graphical representations illustrating stages in a method for identifying outlier waveforms according to another embodiment of the invention.

DETAILED DESCRIPTION

The invention will now be described in further detail by reference to the drawings, which illustrate alternative embodiments of the invention. The drawings are diagrammatic, showing features of the invention and their relation to other features and structures, and are not made to scale. For improved clarity of presentation, in the FIGs. illustrating embodiments of the invention, features corresponding to features shown in other drawings are not all particularly renumbered, although they are all readily identifiable in all the FIGs.

Figure 1A:
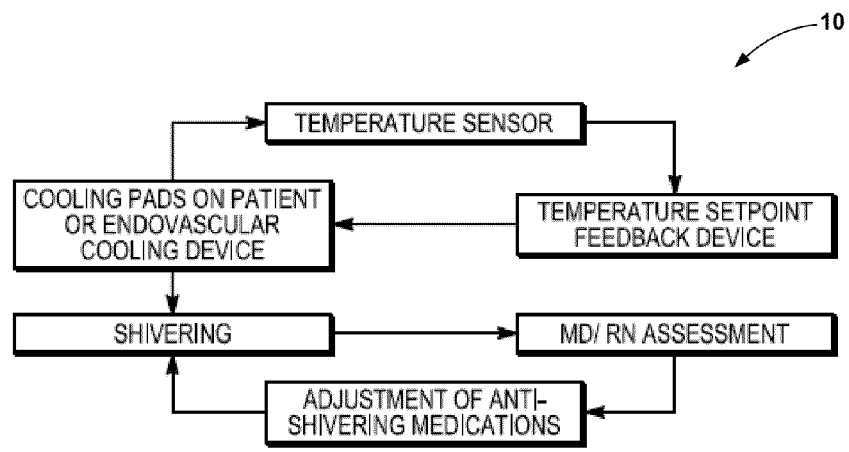
FIG. 1A is a block diagram illustrating a conventional approach to therapeutic temperature management and treatment of shivering.

Referring to FIG. 1A, there is shown generally at 10 a conventional approach to therapeutic temperature management in a patient requiring maintenance of normothermia or induction of hypothermia. According to a conventional approach, a temperature sensor senses the patient's core temperature. A cooling device, such as cooling pads or an endovascular cooling device, effects a lowering of the core temperature. Therapeutic cooling of the patient may be controlled by a feedback system, in which the temperature sensor is operatively connected to a temperature set point feedback device and the temperature set point feedback device is operatively connected to the cooling device. As the patient's core temperature, sensed by the temperature sensor, falls below a selected set point, the feedback device signals the cooling device to reduce cooling; as the temperature at the probe rises above the set point, the feedback device signals the cooling device to increase cooling. That is, deviations of the patient's core temperature upward from a desired temperature set point trigger cooling of the core, and deviations downward from the desired temperature set point trigger reduced cooling or warming of the core. The resulting changes in the patient's core temperature are sensed at the temperature sensor. When shivering is observed by attending medical personnel (such as an attending doctor or nurse), an assessment is made by the personnel and, if judged to be indicated, a counterwarming therapy or other anti-shivering measures such as medications may be adjusted or initiated.

Figure 1B:
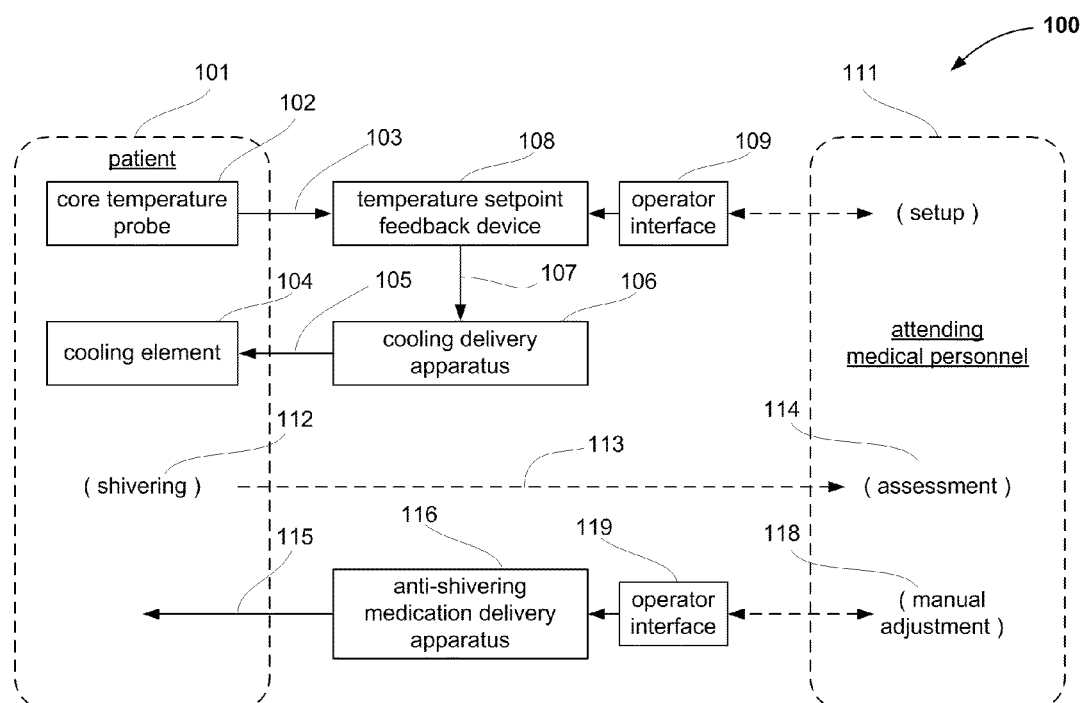
FIG. 1B is a block diagram illustrating a conventional approach to therapeutic temperature management and treatment of shivering.

Such a conventional system is illustrated in further detail generally at 100 in FIG. 1B. In this FIG., broken line 101 outlines features associated with the patient, and broken line 111 outlines activities associated with attending medical personnel. A core temperature probe 102 is placed at a site on or in the patient's body, to sense the patient's core temperature. Various temperature probes are characterized by their placement site, and typical temperature probes include rectal, (urinary) bladder, esophageal, or endovascular probes. A cooling device 104 is placed at one or more sites on or in the patent's body, to effect a lowering of the core temperature. Various cooling apparatus are in common use; particular examples include a cooling delivery apparatus 106 that cools a delivery fluid and delivers it to the cooling device 104 by way of a conduit 105. Typical cooling devices include a cooling blanket, or cooling pads, or an endovascular cooling catheter; and typical cooling delivery apparatus include a cooling fluid reservoir, and a fluid pump, by which cooling fluid is circulated from the reservoir through the cooling devices and back to the reservoir. Therapeutic cooling of the patient may be controlled by a feedback system, in which the temperature probe 102 is operatively connected (103) to a temperature set point feedback device 108 and the temperature setpoint feedback device 108 is operatively connected (107) to the cooling delivery apparatus 106. Attending medical personnel select system settings, such as a target temperature setpoint, using an operator interface 109 associated with the temperature setpoint feedback device. As the patient's core temperature, sensed at the probe 102, falls below the selected target setpoint, the feedback device 108 signals the cooling apparatus 106, 105, 104) to reduce cooling; as the temperature at the probe 102 rises above the selected target set point, the feedback device 108 signals the cooling apparatus to increase cooling. That is, deviations of the patient's core temperature upward from a selected temperature set point trigger cooling of the core, and deviations downward from the selected temperature set point trigger reduced cooling or warming of the core. The resulting changes in the patient's core temperature are sensed at the temperature probe 102.

To induce normothermia in a patient having an elevated core temperature (fever), the set point at the temperature feedback device may be set to within the normal body temperature of the patient (about 37° C. for a human). To induce hypothermia in a patient in need of hypothermia treatment, the set point at the temperature feedback device may be set to a temperature below the patient's normal body temperature (for mild hypothermia, for example, to a temperature in a range about 32° C. to about 34° C. for a human).

As the core is cooled, a shivering response 112 may set in. For humans, shivering may be initiated as the core temperature falls, and may intensify during active induction of hypothermia. Shivering may be most intense during maintenance of normothermia in a patient who is trying to mount a fever. Shivering interferes with the therapeutic cooling process. In a conventional approach, shivering is controlled by administration of anti-shivering medications, and typically administration of the medication is initiated before cooling has begun, or before the core temperature has been cooled to a point at which shivering would be expected. The anti-shivering medication is delivered to the patient through a conduit 115 from a medication delivery apparatus 116, which is operable by attending medical personnel by way of an operator interface 119. The medication may be delivered by a syringe-and-needle device, or a syringe-and-vascular intubation, for example.

Typically in a conventional approach, the effectiveness of the anti-shivering medication is monitored by direct observation (113) of the patient and assessment 114 by attending medical personnel 111. When shivering 112 is observed (113), an adjustment 118 in the anti-shivering medication may be ordered, to attempt to reduce the shivering. Additional adjustment may be made following further observation and assessment.

Figure 2A:
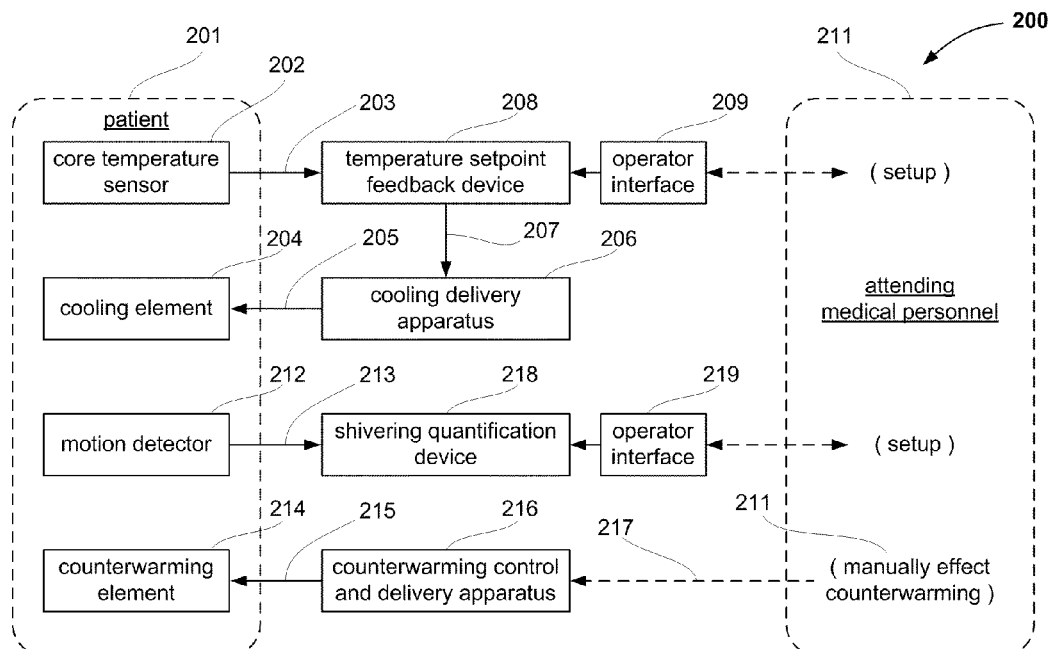
FIG. 2A is a block diagram illustrating an approach to therapeutic temperature management according to an embodiment of the invention.

FIG. 2A illustrates generally at 200 a therapeutic temperature management system according to an embodiment of the invention, in which a counterwarming system quantifies shivering, and counterwarming is effectuated accordingly. In this embodiment therapeutic cooling is controlled by a feedback system, generally as described above with reference to FIG. 1B; but here shivering control differs from that in the conventional approach.

In FIG. 2A, broken line 201 outlines features associated with the patient, and broken line 211 outlines activities associated with attending medical personnel.

The therapeutic cooling system in this embodiment is substantially similar to that employed in a conventional treatment approach. A core temperature probe 202 is placed at a site on or in the patient's body, to sense the patient's core temperature, and a cooling device 204 is placed at one or more sites on or in the patent's body, to effect a lowering of the core temperature. Various temperature probes are characterized by their placement site, and typical temperature probes include rectal, (urinary) bladder, esophageal, or endovascular probes. Various cooling apparatus are in common use; particular examples include a cooling delivery apparatus 206 that cools a delivery fluid and delivers it to the cooling device 204 by way of a conduit 205. Typical cooling devices include a cooling blanket, or cooling pads, or an endovascular cooling catheter; and typical cooling delivery apparatus include a cooling fluid reservoir, and a fluid pump, by which cooling fluid is circulated from the reservoir through the cooling devices and back to the reservoir. Therapeutic cooling of the patient may be controlled by a feedback system, in which the temperature probe 202 is operatively connected (203) to a temperature set point feedback device 208 and the temperature setpoint feedback device 208 is operatively connected (207) to the cooling delivery apparatus 206. Attending medical personnel 211 select system settings, such as a target temperature setpoint, using an operator interface 209 associated with the temperature setpoint feedback device. As the patient's core temperature, sensed at the probe 202, falls below the selected target setpoint, the feedback device 208 signals the cooling apparatus 206, 205, 204) to reduce cooling; as the temperature at the probe 202 rises above the selected target set point, the feedback device 208 signals the cooling apparatus to increase cooling. That is, deviations of the patient's core temperature upward from a selected temperature set point trigger cooling of the core, and deviations downward from the selected temperature set point trigger reduced cooling or warming of the core. The resulting changes in the patient's core temperature are sensed at the temperature probe 202.

To induce normothermia in a patient having an elevated core temperature (fever), the set point at the temperature feedback device may be set to within the normal body temperature of the patient (about 37° C. for a human). To induce hypothermia in a patient in need of hypothermia treatment, the set point at the temperature feedback device may be set to a temperature below the patient's normal body temperature (for mild hypothermia, for example, to a temperature in a range about 32° C. to about 34° C. for a human).

As the core is cooled, a shivering response may set in. For humans, shivering may be initiated as the core temperature falls, and may intensify during active induction of hypothermia. Shivering may occur during maintenance of normothermia in a patient who is trying to mount a fever. According to embodiments of the invention, one or more shivering sensor elements (motion detectors) 212 are placed at sites overlying a muscle mass that is susceptible to shivering. The motion detector element(s) may sense movement of the muscles mass directly; they may for example include an accelerometer or other movement or vibration detection system. Or, the motion detector element may detect the motion indirectly; it may for example include one or more electrodes such as, for example, surface electrodes, subcutaneous electrodes, or intramuscular electrodes; and the shivering sensor elements may include for example any of a variety of electrodes which measure electrical activity in the muscle mass, such as electrodes that may be employed for recording ECG/EMG or EMG.

Where direct sensing of movement of the muscle mass is desired, suitable detector include any of various vibration monitors, and the detector may be selected according t its known performance parameters (such as for example sensitivity, amplitude, frequency range). These may measure displacement, velocity, and/or acceleration. Suitable sensors include, for example, piezoelectric displacement transducers (doubly integrated accelerometers), electromagnetic velocity sensors, piezoelectric velocity sensors (internally integrated accelerometers), and piezoelectric accelerometers. Piezoelectric sensors may be useful, and piezoelectric accelerometers may be particularly suitable. The sensor may include a microelectromechanical system (MEMS) device, for example; and may be sensitive to acceleration in one, or two (2D), or three dimensions (3D). Suitable motion sensors are available from, for example, Cole-Parmer, Vernon, Ill. 60061 USA; and for example, a small format accelerometer such as a "9000 Series Accelerometer", marketed by Vibra-Metrics, Princeton Jct., N.J. 08550, USA, may be suitable. The motion detector (for example, accelerometer) can be held in place on the patient's skin by, for example, an elastic strap, or an adhesive, such as a hydrogel adhesive.

Where it is desired to measure movement of the muscle mass indirectly, by electrodes, any of a broad choice of commercially available ECG or EMG electrodes may be used, for example disposable or reusable adhesive or adherent ECG or EMG or disc-type electrodes or needle monopolar or bipolar EMG electrodes.

A shivering quantification device 218 is operatively connected (213) to the motion detector 212. The shivering quantification device includes a computer configured to process and store data corresponding to electrical signals received from the motion detector, and to generate shivering quantification output, for example as described more fully below. Attending medical personnel select shivering quantification system settings using an operator interface 219 associated with the shivering quantification device 218. In this embodiment, the operator interface 219 may provide an output to the attending personnel of the result of shivering quantification; the output may include a visual display, or a sound, for example. Preferably the output is a real-time or near real-time representation of the condition of shivering in the patient, for example in graphical and/or numerical form. In embodiments in which mechanical and electrical shivering detection are both employed, the data from the two types of detection system may be integrated or used in several ways. For example, the average of the two signals may be displayed or used, or change in measurements from one method can be used to validate changes in the other. Discrepancies between the two signals, for example a difference in values between the two systems by a preset or user-adjustable difference or a loss of correlation between the trend in the two signals, can trigger re-analysis or notification of the attending medical personnel 211 by way of the operator interface 219.

As noted above, shivering interferes with the therapeutic cooling process, and is potentially deleterious to the patient. Reduction of shivering can significantly improve therapeutic induction of hypothermia or maintenance of normothermia. Shivering may be controlled by application of, or by activation or adjustment of, one or more counterwarming elements, or by administration of an anti-shivering medication.

In the example illustrated in FIG. 2A, one or more counterwarming elements 214 are placed on exposed areas of the patient's body. Suitable areas for the counterwarming elements include the hands, the feet, and the ears, for example, or other areas that are not in use for core warming. Optionally, one or more warming blankets may be placed above, or below, or above and below the patient's body, in contact with skin areas not actively being cooled. The counterwarming elements 214 heat the areas of the body that they contact, resulting in an inhibition of shivering. The counterwarming elements may be heating pads or heating blankets, which may be activated by an electrical current in resistive conductors, or by a flow of fluid in tubing, for example. A counterwarming control and delivery apparatus 216 is operatively connected (215) to activate the counterwarming elements 214.

Attending medical personnel, alerted to a shivering condition by the output from the shivering quantification device, can in response manually effect or modify counterwarming (211) by increasing or decreasing warming by the counterwarming element 214, for example by adjustment or activation (217) of the counterwarming control and delivery apparatus 216. Changes in the degree of shivering result from changes in the core temperature or from changes effected by the counterwarming element 214. If the counterwarming is effective to reduce shivering, a reduction in shivering is provided to attending personnel as an output of the real-time or near real-time shivering quantification; if the counterwarming is insufficient to reduce shivering, attending personnel may make further adjustments, until the shivering quantification output indicates that shivering has subsided to an acceptable level.

Figure 2B:
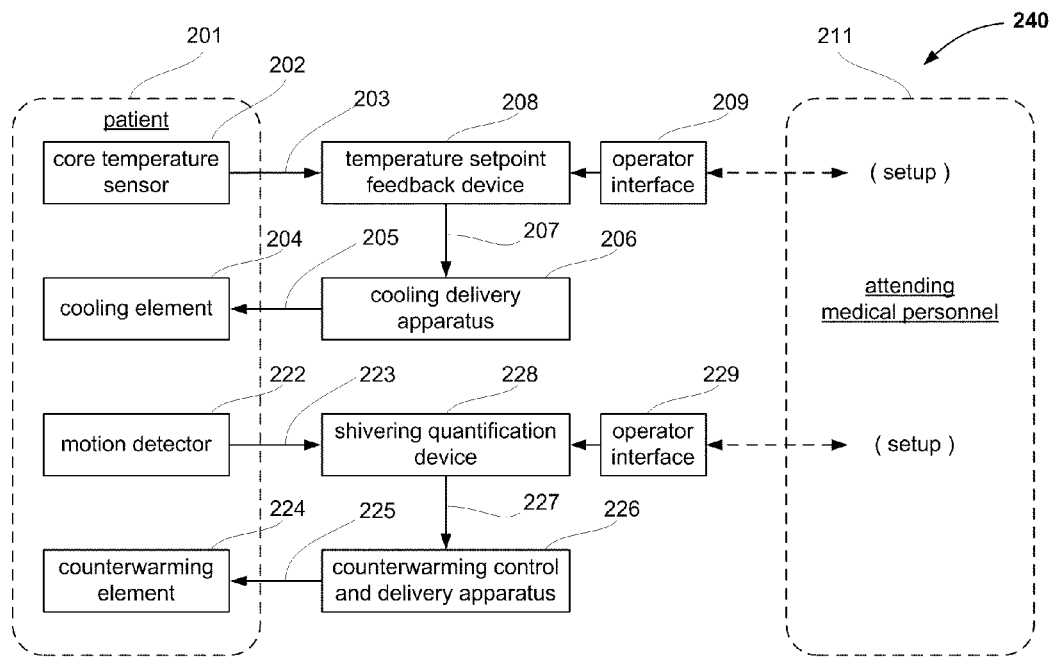
FIG. 2B is a block diagram illustrating an approach to therapeutic temperature management according to another embodiment of the invention.

In some embodiments of a temperature management system, as shown for example generally at 240 in FIG. 2B, shivering in the patient is controlled by a feedback system. In FIG. 2B, broken line 201 outlines features associated with the patient, and broken line 211 outlines activities associated with attending medical personnel. The therapeutic cooling system in this embodiment is substantially similar to that described with reference to FIG. 2A. In this embodiment, control of counterwarming is automated. Here, as in the example of FIG. 2A, shivering sensor elements (motion detectors) 222 are placed at sites on or in the patient's body selected as suitable for detection of shivering, usually at muscle masses that are susceptible to shivering. The motion detector may include one or more electrodes; or, the motion detector may include one or more vibration detection sensors (for example, accelerometers), or the motion detector may include both electrodes and vibration detection sensors. A shivering quantification device 228 is operatively connected (223) to the motion detector 222. The shivering quantification device includes a computer configured to process and store data corresponding to electrical signals received from the motion detector, and to generate shivering quantification output, for example as described more fully below. Attending medical personnel select shivering quantification system settings using an operator interface 229 associated with the shivering quantification device 228. Also in the example illustrated in FIG. 2B, one or more counterwarming elements 224 are placed on exposed areas of the patient's body, generally as described above with reference to FIG. 2A. A counterwarming control and delivery apparatus 226 is operatively connected (225) to activate the counterwarming elements 224.

In this embodiment, as in the example of FIG. 2A, attending medical personnel select shivering quantification system settings using an operator interface 229 associated with the shivering quantification device 228. The operator interface 229 may provide an output to the attending personnel of the result of shivering quantification; the output may include a visual display, or a sound, for example. Preferably the output is a real-time or near real-time representation of the condition of shivering in the patient. Additionally, in this embodiment, the shivering quantification device 228 provides (227) an output to the counterwarming control and delivery apparatus 226. The counterwarming control and delivery apparatus 226 includes a computer configured to process and store data corresponding to electrical signals received from the shivering quantification device 228, and to generate counterwarming instructional output (227) to the counterwarming control and delivery apparatus 226, for example as described more fully below. This output is correlated to the degree of shivering. The counterwarming control and delivery apparatus 226 can in response to the output signal (227) from the shivering quantification device 228 automatically effect or modify counterwarming by increasing or decreasing warming by the counterwarming element 224. Changes in the degree of shivering result from changes in the core temperature or from changes effected by the counterwarming element 224. If the counterwarming is effective to reduce shivering, a reduction in shivering is sent to the counterwarming control and delivery apparatus 226 as an output of the real-time or near real-time shivering quantification by the shivering quantification system (222, 223, 228), and the counterwarming is automatically adjusted accordingly; if the counterwarming is insufficient to reduce shivering, a lack of reduction in shivering is signaled by the shivering quantification system (222, 223, 228) to the counterwarming control and delivery apparatus 226, which may automatically make further adjustments, until the shivering quantification output indicates that shivering has subsided to an acceptable level.

Figure 2C:
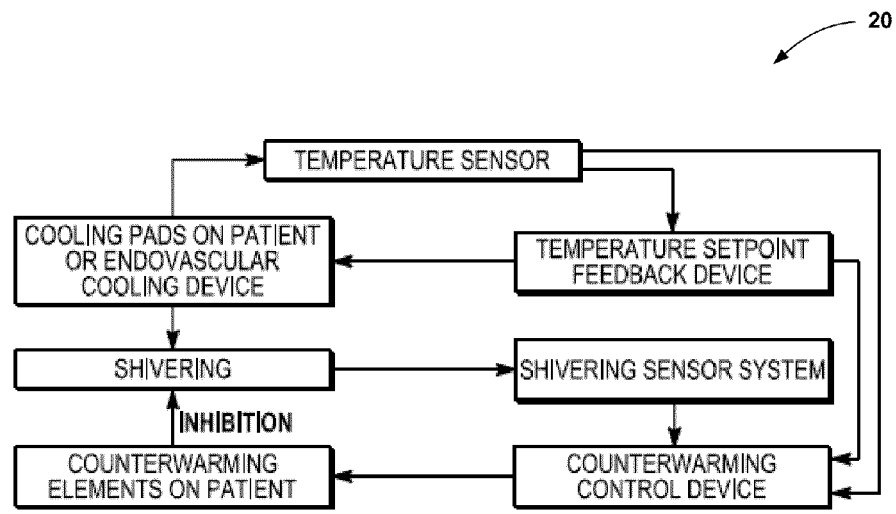
FIG. 2C is a block diagram illustrating an approach to therapeutic temperature management according to another embodiment of the invention.

A more complex therapeutic temperature management system according to an embodiment of the invention is shown generally at 20 in FIG. 2C. In this embodiment, as in the example of FIG. 2B, both therapeutic cooling and counterwarming are controlled by feedback, and here additional feedback loops are optionally available. In such embodiments, a temperature sensor senses the patient's core temperature. A cooling device, such as cooling pads or an endovascular cooling device, effects a lowering of the core temperature. Therapeutic cooling of the patient may be controlled by a feedback system, in which the temperature sensor is operatively connected to a temperature set point feedback device and the temperature set point feedback device is operatively connected to the cooling device. As the patient's core temperature, sensed by the temperature sensor, falls below a selected set point, the feedback device signals the cooling device to reduce cooling; as the temperature at the probe rises above the set point, the feedback device signals the cooling device to increase cooling. That is, deviations of the patient's core temperature upward from a desired temperature set point trigger cooling of the core, and deviations downward from the desired temperature set point trigger reduced cooling or warming of the core. The resulting changes in the patient's core temperature are sensed at the temperature sensor. A detector at the patient sends a signal to a shivering sensor system, which processes the signal and sends a counterwarming instruction signal to a counterwarming control device. The counterwarming control device in turn sends a signal to counterwarming elements at the patient to initiate or adjust the amount of counterwarming. Effective counterwarming inhibits shivering.

Figure 2D:
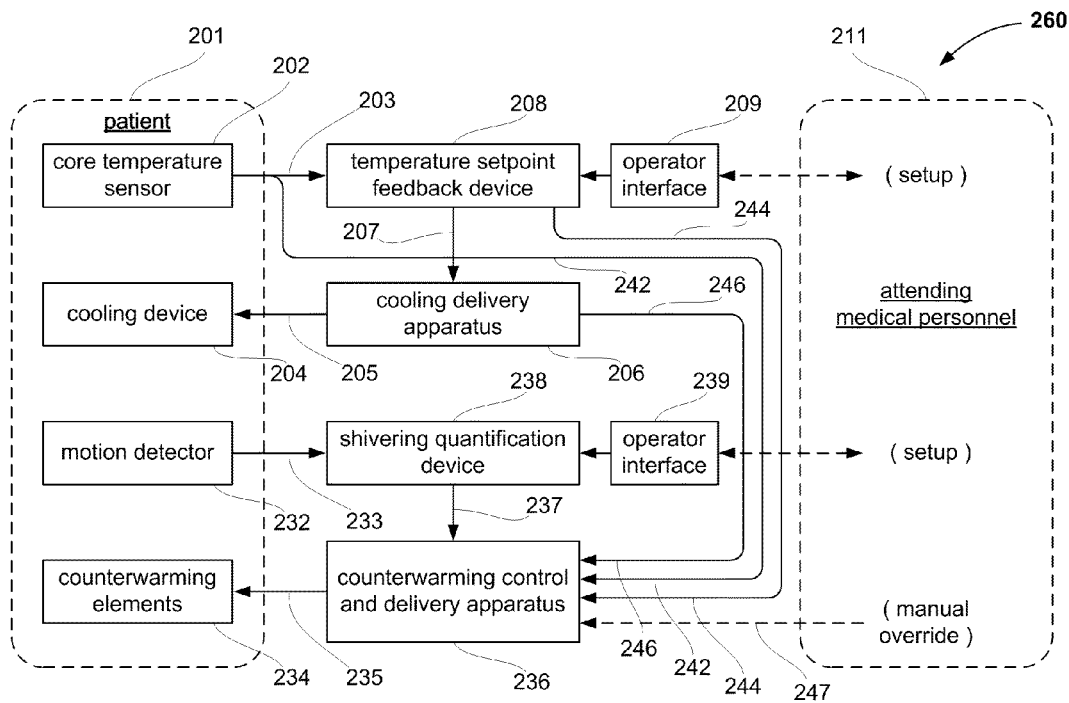
FIG. 2D is a block diagram illustrating an approach to therapeutic temperature management according to another embodiment of the invention.

An example of such an embodiment is shown generally at 260 by way of example in FIG. 2D, in which broken line 201 outlines features associated with the patient, and broken line 211 outlines activities associated with attending medical personnel. The therapeutic cooling system and the counterwarming system in this embodiment are substantially similar to those described with reference to FIG. 2B. Particularly, here, as in the example of FIG. 2B, a shivering sensor element (motion detector) 232 is placed at a site on or in the patient's body selected as suitable for detection of shivering, usually at a muscle mass that is susceptible to shivering. The motion detector may include one or more electrodes; or, the motion detector may include one or more vibration sensors (for example, an accelerometer). A shivering quantification device 238 is operatively connected (233) to the motion detector 232. The shivering quantification device includes a computer configured to process and store data corresponding to electrical signals received from the motion detector, and to generate shivering quantification output, for example as described more fully below. Attending medical personnel select shivering quantification system settings using an operator interface 239 associated with the shivering quantification device 228. Also in the example illustrated in FIG. 2D, one or more counterwarming elements 234 are placed on exposed areas of the patient's body, generally as described above with reference to FIG. 2B. A counterwarming control and delivery apparatus 236 is operatively connected (235) to activate the counterwarming elements 234.

Additionally, in the example illustrated in FIG. 2D, the counterwarming control and delivery apparatus 236 is configured to receive signals from one or more other components of the apparatus; for example: the counterwarming control and delivery apparatus may be operatively connected (242) to receive electrical signals from the core temperature sensor 202, and/or operatively connected (244) to receive data signals from the temperature setpoint feedback device 208, and/or operatively connected 246) to receive data signals from the cooling delivery apparatus 206.

The three general feedback mechanisms by which the counterwarming control and delivery apparatus 236 may initiate and/or regulate the degree or pattern of counterwarming may be used in concert as shown diagrammatically in FIG. 2D; alternatively the feedback mechanisms may be used in various embodiments alone or in any combination. For example, a counterwarming control and delivery apparatus 236 may be set up to respond solely to the degree of cooling being applied by the cooling delivery apparatus 206, without regulation by the other feedback mechanisms. Similarly, any combination of the three feedback mechanisms may be used alone or in any combination of two or three feedback mechanisms. In some embodiments, for example, the signals received by the counterwarming control and delivery apparatus 236 from the cooling delivery apparatus 206 and the temperature set point feedback device 208 by way of their operative connections (246), (244) with the counterwarming control and delivery apparatus 236 are set up in such a way that the counterwarming control and delivery apparatus 236 and the cooling delivery apparatus 206 are part of one unit of operation. In other embodiments, for example, the counterwarming control and delivery apparatus 236 is not part of the same unit of operation as the cooling delivery apparatus 206 but is instead connected by way of operative connections (246), (244) to any separate cooling delivery apparatus 206 capable of sending digital or analog signals representing patient temperature and/or extent of core cooling energy being employed to form operative connections (246), (244) with an external counterwarming control and delivery apparatus 236 such that these connections may be used to regulate any or all of the functions of the counterwarming control and delivery apparatus 236 as described herein. In some embodiments, for example, patient temperature data may be acquired separately by direct operative connection of a temperature probe to the counterwarming control and delivery apparatus 236 with or without use of additional temperature data from an operatively connected cooling delivery apparatus 206.

Additionally, the counterwarming control and delivery apparatus 236 may optionally be configured to receive input (247) directly from attending medical personnel, in the event manual override of input to the counterwarming control by the shivering quantification device is indicated or desired. Manual override may be indicated where, for example, under particular circumstances, combined ECG+EMG data may be difficult to process; or where, for example, the shivering quantification appears to attending personnel to be spurious. In such a situation the attending personnel may wish to manually enter a degree of shivering, based on a clinical scale, which may be a standardized clinical scale. (See, e.g., *Stroke*, Vol. 39 (12) pages 3242-47, December 2008, EPub Oct. 16, 2008). Where manual override of the shivering quantification is employed, feedback based on cooling intensity or core temperature may still be employed automatically by the counterwarming controller at the discretion of the attending medical personnel 211 by way of the operator interface 239. Manual override by way of the operator interface 239 or automatic override by feedback mechanism can be triggered when prolonged higher intensity counterwarming has been applied, in order to prevent the possibility of thermal injury.

According to various embodiments of the invention the shivering control system can regulate the intensity, the timing and/or the pattern of application of counterwarming in a dynamic fashion based on data related to the intensity of core cooling, or measured shivering, or patient core temperature, or to any combination of any two or more of these factors.

Figure 3:
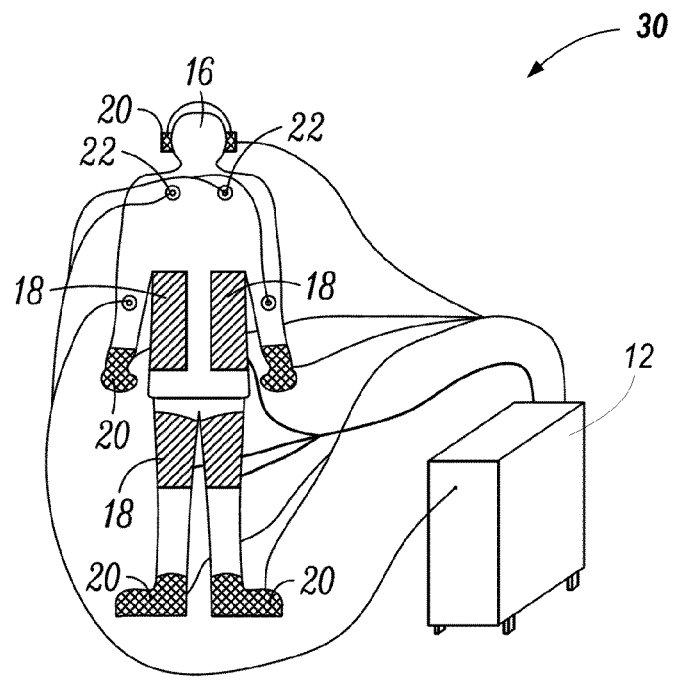
FIGS. 3 and 4 are diagrammatic sketches showing deployment of temperature management apparatus according to an embodiment of the invention.
Figure 4:
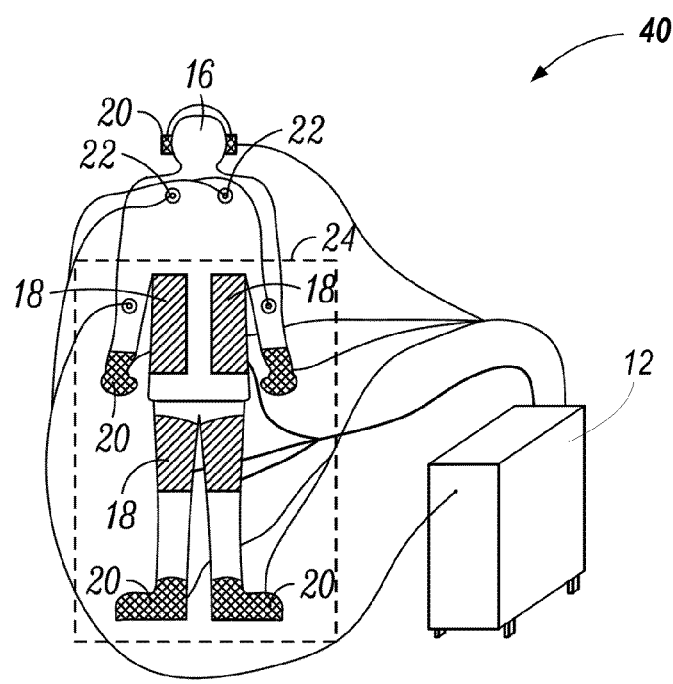

Embodiments of a system according to the invention are illustrated diagrammatically generally at 30 and 40 in FIGS. 3 and 4, as applied to a patient 16 in need of normothermia maintenance or induced hypothermia. Typically the patient is in a supine position. In these embodiments an integrated control device (a suitably configured computer) 12 is operatively connected to cooling pads 18, counterwarming elements 20, and shivering sensor elements 22, which are placed on suitable sites on the patient's body. Additionally, a core temperature probe (not shown in the FIGs.) is connected to the integrated control device 12. Optionally, a warming blanket 24 may be placed over and/or under the patient, as shown in FIG. 4.

The integrated control device 12 is configured and programmed to receive and/or send electrical signals from/to the respective sensors, elements, probe and pads on and in the patient's body. For example, the integrated control device may receive electrical signals from the shivering sensor elements and the core temperature probe; and, for example it may send electrical instruction signals to the cooling pads and counterwarming elements. The integrated control device 12 may include various components, including one or more microprocessors and memory devices, that receive and process various received signals. Various components of the integrated control device 12 may be configured to communicate electrically with one another and to process received signals. For example, a counterwarming controller component may be configured to receive and process electrical signals from a temperature set point controller component. All the data and signal processing functions may be carried out in the integrated control device, as suggested by the FIGs.; optionally, at least a portion of the data processing or signal processing functions may be carried out in hardware (microprocessor and/or memory) situated on or in one or more of the sensor elements.

The active counterwarming elements are used to warm various body regions such as the hands, feet, ears, upper back, posterior neck, or other exposed regions not being used as a site for core cooling. Hand warming elements may be in a glove form that encloses each of the fingers separately, in a mitten form that encloses four fingers together, or in a form of a wrap around the hand. Variations of the shape of the hand warming elements may be used to allow for appropriate access to sites frequently used in critical care, such as for example the region of the radial artery in the wrist. Foot warming elements may be applied to the feet selectively (similar in shape to shoes) or to the feet and ankles together (similar in shape to socks). Ear warming elements may take a form similar to earmuffs, or may take the form of a small warming blanket applied to the ears and neck area, for example. Other areas are warmed by warming blankets or small pads that are selectively applied or cover a larger area of the patient's body or are placed under the patient.

Placement and analysis of the shivering sensor elements is customized to the needs of the particular application.

Figure 5A:
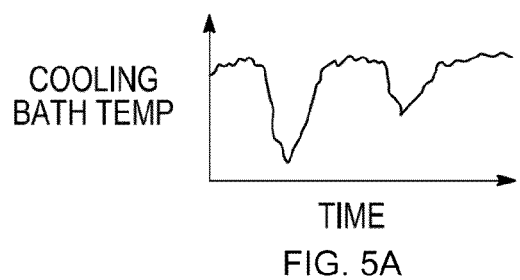
FIGS. 5A and 5B are idealized graphical representations illustrating a relationship over time between cooling bath temperature (FIG. 5A) and warming element temperature (FIG. 5B).
Figure 5B:
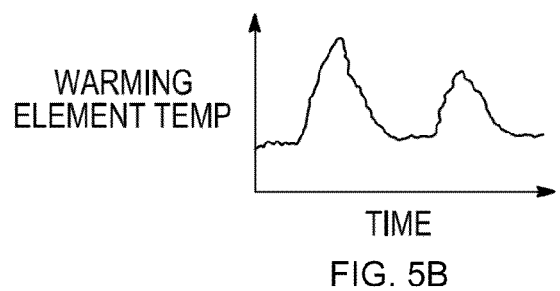

Generally, as illustrated diagrammatically in FIGS. 5A and 5B, the counterwarming element temperature is regulated roughly in proportion to the inverse of the cooling element temperature as measured, for example, at the bath of cooling liquid flowing to the patient cooling elements. That is, as the cooling element (cooling bath) temperature falls, a feedback loop causes the counterwarming temperature to rise.

Figure 6A:
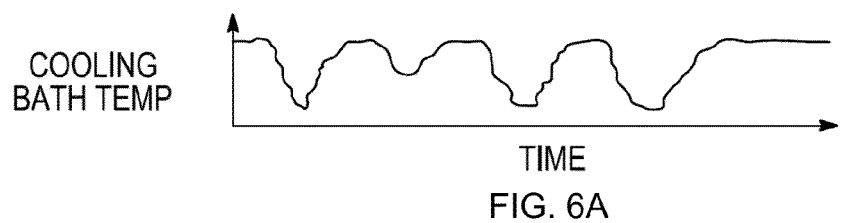
FIGS. 6A, 6B and 6C are idealized graphical representations illustrating an effect of shivering (FIG. 6B) on a relationship over time between cooling bath temperature (FIG. 6A) and warming element temperature (FIG. 6C).
Figure 6B:
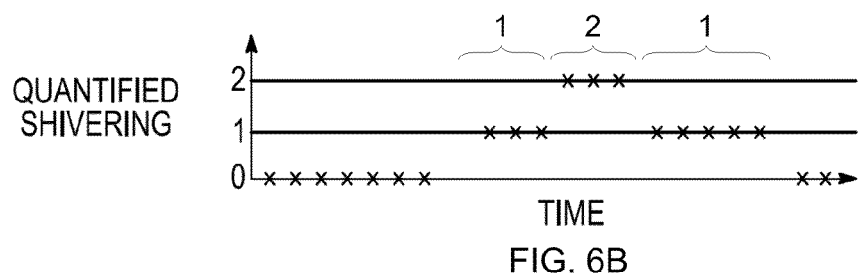
Figure 6C:
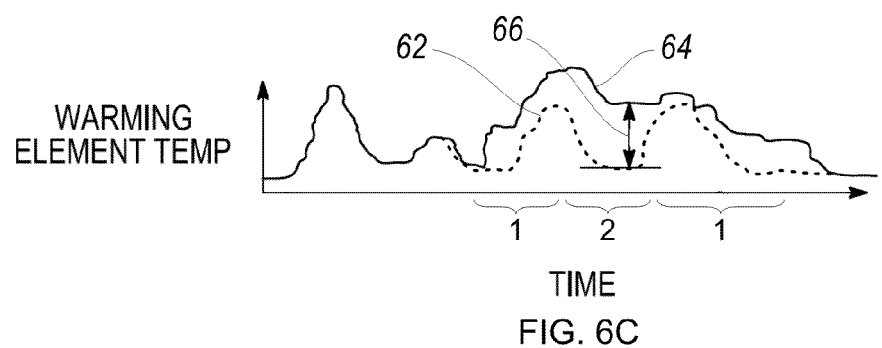

As illustrated diagrammatically in FIGS. 6A, 6B and 6C, the warming element temperature (FIG. 6C) can according to the invention be adjusted upward during periods of shivering (FIG. 6B). FIG. 6A shows measured changes in the cooling bath temperature. FIG. 6B shows a sample plot of shivering over the same time period, quantified in this example according to the invention at three score levels: a level 0 corresponding to no shivering or shivering less than a threshold level; a level 1 corresponding to mild shivering; and a level 2 corresponding to vigorous shivering. In other embodiments, shivering intensity may be encoded as a continuous variable or as a score variable with more levels. FIG. 6C shows counterwarming element temperature over the same time period. As noted above, in the absence of regulation the counterwarming element temperature generally mirrors the cooling bath temperature. The broken line 62 shows how counterwarming element temperature unregulated by shivering would appear, generally mirroring the plot of cooling bath temperature in FIG. 6A. The plot 64 shows a regulated counterwarming temperature, in which the warming is adjusted upward during periods of shivering. The regulated counterwarming element temperature over the same time period is adjusted upward during level 1 shivering, adjusted further upward during level 2 shivering, adjusted downward during a subsequent period of reduced (level 1) shivering, and adjusted further downward (mirroring the cooling bath temperature plot) during a subsequent period of level 0 (no or undetected) shivering. Particularly, for example, the counterwarming temperature would in the absence of shivering-based regulation have returned to off or to a baseline level during the interval indicated by the bracket labeled 2; instead, because maximum shivering is detected during this interval, the adjusted counterwarming temperature remains high, as indicated by the double arrow at 66.

Quantification of shivering according to various embodiments of the invention may include some or all of the following stages and components.

For electrode-based detection, two or more electrodes may be arrayed to obtain the surface EMG data. In some applications the shivering sensor elements may include surface electrodes, such as for example ECG or EMG electrodes; and they may be applied to any exposed skin region overlying a muscle group engaged in shivering. Or, in some applications, needle EMG electrodes may be used instead of surface ECG electrodes to detect shivering at a higher level of sensitivity.

The data processing algorithm to selectively enhance the shivering EMG component of the ECG and EMG data may be set up in a customizable fashion: complete cardiac cycles of ECG data can be analyzed, or specific segments of ECG tracings can be analyzed after alignment so that regions having minimal ECG data elements (such as the S-T segment and the region between the end of the T wave and the start of the P wave) are selectively analyzed.

As in known ECG measurement using surface electrodes, voltage differences from pairs of surface ECG electrodes may be measured by means of a standard ECG amplifier with an appropriate reference and ground. In a shivering patient, the measured voltage tracing from any pair of ECG surface electrodes overlying muscle groups involved in shivering will be a superimposition of ECG and shivering electromyogram (EMG) tracings. The mixed ECG+EMG tracing may be digitized by standard analog-to-digital conversion at a sampling rate that adequately records the higher frequency EMG data.

Using standard techniques for automated digital signal detection of the characteristic components of the ECG, such as the QRS complex, several complete cardiac cycles of ECG+EMG data may be sampled and stored in separate digital buffers.

Using standard techniques for automated digital signal detection of premature ventricular complex (PVCs) or other examples of atypical QRS morphology, cardiac cycles that include a QRS morphology that is an outlier compared to the baseline are identified and omitted from the analysis. Standard techniques for distinguishing atypical QRS morphology are known in the prior art and include, for example, detection of QRS complexes with longer duration than the baseline duration, detection of QRS complexes with a different electrical vector (the ECG 'axis') from that of the baseline QRS, and detection of QRS complexes with higher amplitude than that of the baseline ECG.

Any of several techniques may be employed to exclude atypical ECG complexes. In some embodiments, in which the desired temporal resolution for shivering quantification allows for averaging of a larger number of complexes, the number of averaged complexes may be increased to minimize or substantially reduce the impact of outlier complexes in the analysis. In such circumstances in which frequent outlier ECG morphologies are identified by the user or by any of the techniques of analysis described or referenced herein, the number of averaged tracings may be increased, manually or automatically, to minimize or substantially reduce the impact of outlier complexes in the analysis.

In some embodiments, a narrow temporal window starting at the peak of the QRS complex (for example, as identified by an amplitude trigger) is captured. The narrow temporal window of captured data, having a time duration representing a small percentage of the total ECG cycle, for example 10 to 50 milliseconds, may be subjected to analysis to discriminate outlier ECG cycles with atypically wide QRS morphologies.

Outlier ECG waveforms may be identified by detecting QRS complexes that are atypically broad. For example, FIGS. 16A-16D show stages in such an approach by measuring the slope of the downward deflection of the QRS. In this approach, analysis of the narrow temporal window including the downslope of the QRS complex includes identification of outliers by determining the slope of the downward deflection of the ECG waveform from the peak of the QRS complex to the end of the narrow temporal window, such that complexes with a downward slope that is insufficiently steep are excluded from analysis. As outlier QRS complexes such as premature ventricular contractions are often of higher amplitude than typical QRS complexes, in some embodiments the amplitudes of the tracings are normalized to the amplitude of a typical QRS complex prior to analysis of the QRS downslope. FIG. 16A shows two cycles, one including a typical QRS complex 162 and the other including an atypical QRS complex 164. A narrow temporal window is set beginning at each QRS peak, as shown at 163 (typical) and 165 (atypical) in FIG. 16B. The portions of the traces within the temporal windows are selected, as shown in FIG. 16C: the window 163 contains the downward deflection 166 of the typical QRS complex, and the window 165 contains the downward deflection 168 of the atypical QRS complex. The slopes of the trace portions can be compared, optionally following normalization of the amplitudes of the defined trace portions, as shown at FIG. 16D. The less steep slope of the trace portion 168' by comparison with the slope of the typical trace portion 166' identifies the QRS complex having the peak 164 as atypical, and the ECG waveform including such an atypical QRS complex is excluded from subsequent analysis. The cutoff slope for exclusion by this technique may be determined based on establishment of the typical ECG downward slope by analysis of average ECG slopes in the patient being monitored, or by user identification of a typical ECG waveform for the patient being monitored. In some embodiments, the user can be presented by means of computer display with a visual array of ECG waveforms from the patient being monitored so that the user may select by computer interface one or more typical ECG waveforms from which the appropriate cut point for the downslope of the QRS complex may be determined.

And, for example, FIGS. 17A-17C show stages in an approach by measuring the width of the QRS complexes at the baseline. ECG complexes having a baseline QRS complex width above a specific cutoff are excluded from subsequent analysis. FIG. 17A shows two cycles, one including a typical QRS complex 172 and the other including an atypical QRS complex 174. The baseline 170b of the ECG trace is established, and the temporal limits of the QRS complexes at the baseline are determined, as shown at FIG. 17B. The time limited typical QRS complex is shown at 176 and the time limited atypical QRS complex is shown at 178. The widths of the QRS complexes at the baseline are then measured, as shown in FIG. 16C: the width of the typical QRS complex 176' is indicated at 172w, and the width of the atypical QRS complex 178' is indicated at 174w. Where a QRS width exceeds a threshold width (as for example width 174w) the ECG trace containing the QRS complex having the wider peak is excluded from subsequent analysis.

The threshold QRS width for exclusion by this approach may be determined by establishing the typical QRS width in the particular patient being monitored. This may be done by analysis of average QRS widths in the patient, or by user identification of a typical ECG waveform for the patient. In some embodiments, the user is presented by means of computer display with a visual array of ECG waveforms from the patient being monitored so that the user may select by computer interface one or more typical ECG waveforms from which the appropriate threshold QRS complex width may be determined. The threshold may be set at some limit, such as one or two standard deviations, for example, above a mean typical waveform width.

In other embodiments, the analysis of the narrow temporal window comprising the downslope of the QRS complex includes identification of outliers by analysis in the frequency domain by means, for example, of Fourier analysis, such as a Fast Fourier Transform (FFT), such that typical narrow complexes are identified as having a high frequency peak and atypical wide complexes lack this high frequency peak. The frequency and amplitude cut points of the Fourier analysis or other frequency analysis used for exclusion of ECG tracings by this method may be determined based on establishment of the typical ECG high frequency peak by analysis of average ECG high frequency peaks or by user identification of a typical ECG waveform. In some embodiments, the user is presented by means of computer display with a visual array of ECG waveforms from the patient being monitored so that the user may select by computer interface one or more typical ECG waveforms, from which the appropriate frequency and amplitude cut points of the Fourier analysis or other frequency analysis may be determined to exclude outlier ECG complexes.

Additionally, standard techniques may be employed for automated digital signal detection of premature ventricular complex (PVCs) or other examples of atypical QRS morphology. Cardiac cycles that include a QRS morphology that is an outlier compared to the baseline may be identified by such established techniques and omitted from subsequent analysis. Standard techniques for distinguishing atypical QRS morphology are known and include, for example, detection of QRS with a different electrical vector (the ECG "axis") from that of the baseline QRS and detection of QRS complexes with higher amplitude than that of the baseline ECG.

The data separation can be carried out on a set of traces, each of which may include a complete cardiac cycle. The EMG data can be separated from the combined ECG+EMG data by aligning the traces based on an easily identified feature of the ECG waveform such as the peak of the QRS complex of the ECG and signal averaging the digitized traces to provide ECG data having a reduced contribution of EMG data, and subtracting the ECG data from the combined EMG and ECG data to yield shivering EMG traces having a reduced contribution of ECG data. A sufficient number of traces are averaged to provide an average EMG signal substantially free of ECG signal components, that is, to reduce the contribution of ECG signal components so that the average EMG signal is substantially uncontaminated by ECG signal components.

Where the data separation is carried out on a set of traces, the signals can be aligned and the separation can be carried out on selected segments of ECG tracings after alignment so that regions with minimal ECG data elements, such as for example the S-T segment and the region between the end of the T wave and the start of the P wave, are selectively analyzed. As described above beginning at paragraph, typical and atypical ECG morphologies can be detected, and cardiac cycles that include outliers (atypical ECG morphologies) can be identified and removed from the analysis. Atypical ECG morphologies can also be excluded from analysis by subtracting stored averaged ECG traces from the same patient under non-shivering conditions, with exclusion of traces that lead to significant residual ECG data (for example, residual voltage amplitude above an adjustable threshold or residual power spectral density in a frequency range lower or higher than that typically associated with shivering energy).

Figure 8A:
FIGS. 8A, 8B, 8C and 8D are idealized graphical representations illustrating stages in a method for shivering quantification according to an embodiment of the invention.

A number (n) of samples of digital ECG+EMG "raw" data (e.g., 10 cardiac cycles) are then automatically aligned in the temporal domain based on the R wave (the positive peak of the QRS complex of the ECG) or other ECG features, as illustrated for 3 cardiac cycles 34 in FIG. 8A.

Figure 8B:
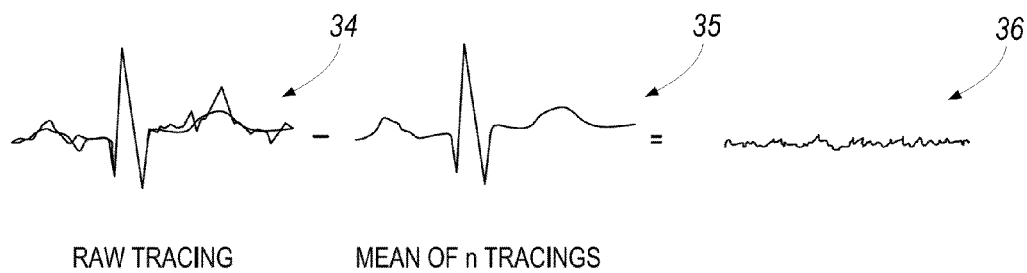

Reference is now made to FIG. 8B. The average ("mean of n tracings" 35) of the aligned n ECG+EMG "raw" data samples 34 is stored in a selected buffer (the "average ECG buffer"). Averaging removes or greatly minimizes the "noise" of shivering EMG and preserves the stereotyped ECG waveform (standard prior art of signal averaging to reduce noise). The difference 36 between each of the n ECG+EMG tracings and the average ECG is stored in another series of buffers ("EMG buffers" 1–n). FIGS. 8A and 8B may be summarized by: (ECG+EMG 34)–(averaged ECG 35)=(EMG 36)

EMG data obtained in the manner described herein yields an EMG tracing with a stable baseline that is uncontaminated by the high amplitude excursions of the ECG. In some embodiments, EMG tracings with an unstable or undulating baseline produced by the presence of atypical ECG complexes in the described averaged signal subtraction process can be identified and excluded from analysis. Traces with such unstable or undulating baselines can be identified in some embodiments by analysis in the frequency domain by means, for example, of Fourier analysis, such as a Fast Fourier Transform ("FFT"), to identify the presence, above a prescribed level, of low frequency (for example, less than 4 Hz) contamination.

The process described above for extracting EMG data from the superimposed ECG +EMG data can be more generally characterized by the process of averaged signal subtraction to largely remove a stereotyped signal (for example, ECG data) from a second signal that lacks the same stereotyped features (for example, EMG data), by the process of subtracting the averaged stereotyped signal after alignment of the superimposed tracings using detectable features of the stereotyped signal. The process of aligning the traces can utilize identifiable features of the stereotyped signal (such as the high amplitude peak of the ECG R wave) or can take advantage of time locking of the stereotyped signal to a measurable event (such as an external stimulus that produces a stereotyped response with a stereotyped time delay) to register the superimposed tracings, the processes usually employed in signal averaging. After alignment of the traces such that averaging the traces largely removes the second signal, this isolated first signal tracing is used to isolate the second signal from the superimposition of the two by the process of wave subtraction.

Figure 7A:
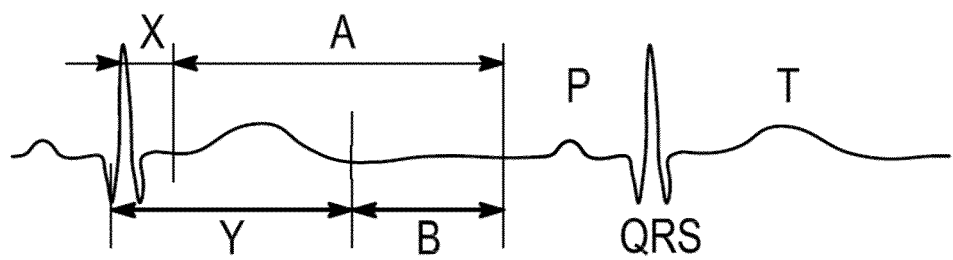
FIGS. 7A, 7B and 7C are idealized graphical representations showing selection of time windows in an ECG for shivering quantification according to an embodiment of the invention.
Figure 7B:
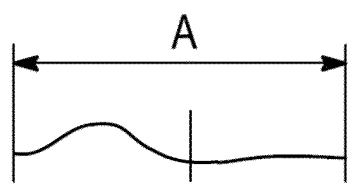
Figure 7C:
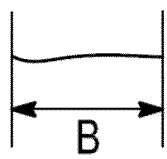

To further minimize contamination of the EMG data stored in the EMG buffers, the (ECG+EMG) and (averaged ECG) tracings can first be 'clipped' in the temporal domain such that a segment of data with minimal ECG voltage deflections is chosen prior to subtraction of (ECG+EMG)–(averaged ECG). Examples of such clipping are illustrated in FIGS. 7A, 7B and 7C. FIG. 7A shows a trace over a time domain including two complete cardiac cycles. This signal may be clipped in the time domain to remove the PQ interval and the QRS complex, leaving the T wave trace and the interval between the T wave and the following P wave, as shown for example at A in FIG. 7B, for analysis. This trace A may be further clipped to remove the T wave, leaving only the interval between the T wave and the following P wave, as shown for example at B in FIG. 7C, for analysis.

Figure 8C:
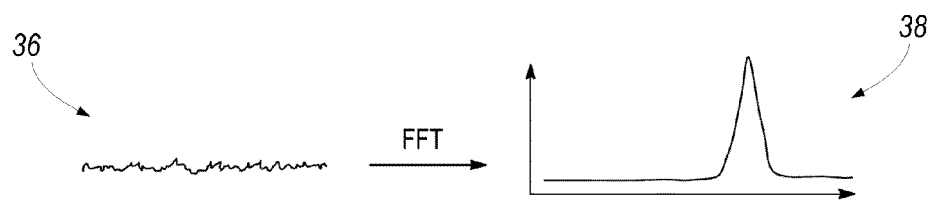
Figure 8D:
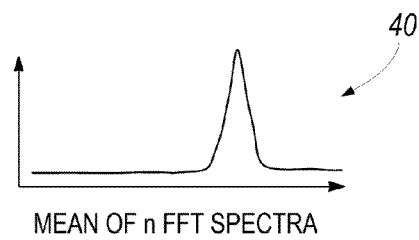

Then a wavelet analysis such as a fast Fourier transform (FFT) may be performed on each of the 1–n EMG buffers, and the resulting power spectrum of each FFT may be stored in another series of buffers ("EMG FFT buffers" 1–n), as illustrated at 38 in FIG. 8C. The 1–n EMG FFT buffers may then be averaged and the result stored in another buffer ("average EMG FFT buffer"), as illustrated in FIG. 8D. In some embodiments, autocorrelation is performed prior to fast Fourier transform (FFT).

Alternatively, the average spectral power of the shivering EMG may be determined by subjecting non-shivering ECG epochs to spectral analysis, and, during monitoring, subjecting shivering ECG cycle epochs (containing ECG and EMG data) to spectral analysis, and then subtracting an average of the non-shivering spectra (ECG only) from an average of the shivering spectra (ECG+EMG) to obtain an averaged EMG spectrum.

Figure 14:
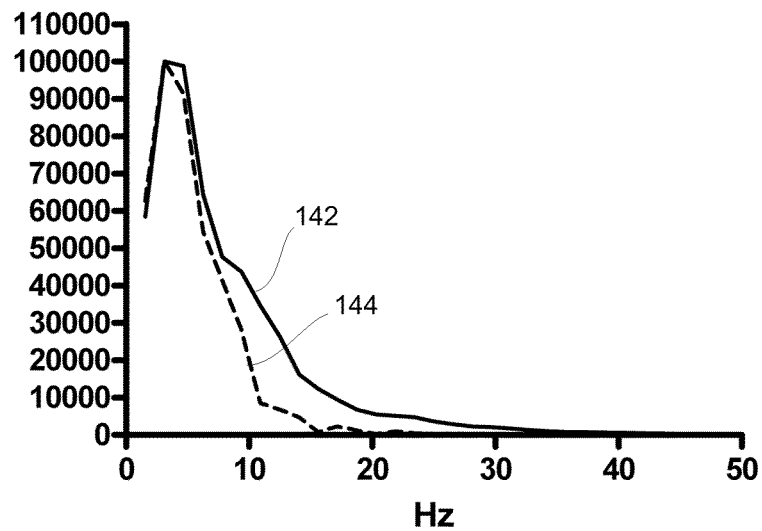
FIGS. 14 and 15 are plots of data, detected in a shivering subject using surface electrodes and analyzed according to another aspect of the invention.
Figure 15:
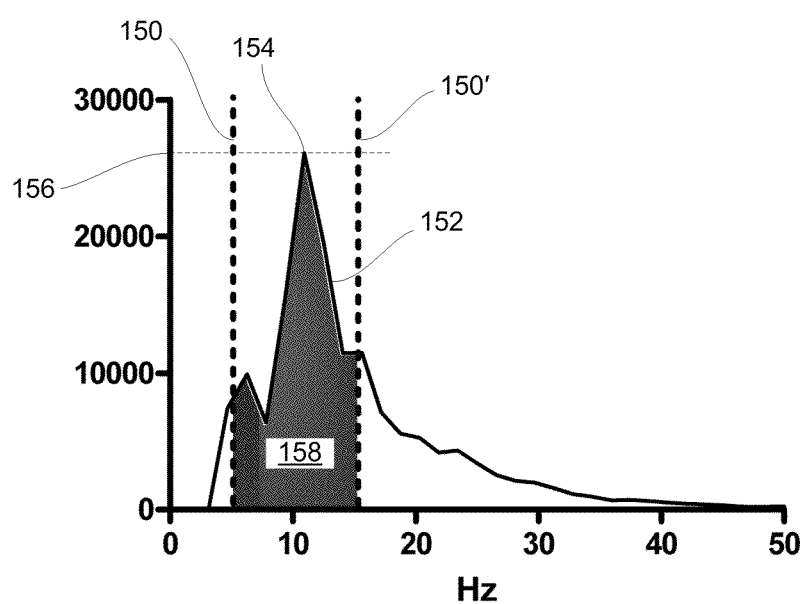

Particularly according to this approach, ECG tracings are first obtained from a subject during non-shivering conditions, such as for example prior to cooling for normothermia or for induced hypothermia. The non-shivering ECG is separated into single ECG cycle epochs as described above and aligned in the temporal domain on specific ECG features such as the peak of the QRS complex. These non-shivering ECG epochs are each subjected to spectral analysis, for example FFT analysis, and the average of n spectral analyses (on n such non-shivering ECG epochs) is then obtained and stored in a digital buffer. When it is desired to monitor shivering in the same subject, this process is repeated: a shivering state (ECG+EMG) tracing is obtained, and is separated into single ECG cycle epochs as described above and aligned in the temporal domain on specific ECG features such as the peak of the QRS complex. These shivering state ECG+EMG epochs are each subjected to spectral analysis, for example FFT analysis, and the average of n spectral analyses (on n such shivering ECG epochs) is then obtained and stored in a different digital buffer. FIG. 14 shows results of such averaged spectral analyses 144 for nonshivering ECG epochs 144, and for shivering state ECG+EMG epochs 142, each epoch corresponding to a cardiac cycle from the peak of the QRS to the region of the T wave. The average spectral analysis (in this example, FFT analysis) from the non-shivering state epochs is subtracted from the average spectral analysis (in this example, FFT analysis) from the shivering state epochs, substantially minimizing the spectral contribution of the average ECG spectral power and revealing the averaged shivering EMG spectrum, with a peak in the appropriate frequency domain for shivering, as shown in FIG. 15. The increased spectral energy around 10 Hz that can be appreciated as a separation of the two lines 142, 144 in FIG. 14 appears in FIG. 15 as a clear peak 154 in this frequency range. The degree of shivering may be quantified according to the height 156 of the peak 154. A frequency range of interest for shivering energy may be isolated, as suggested by the vertical lines 150 and 150', defining a region of interest 158 for shivering energy, and the degree of shivering may be quantified by, for example, the area under the curve 152 in this region, and/or by the peak of the curve 152 in this region.

The average spectral power of the shivering EMG obtained by any method described above may be used alone or in combination to quantify shivering intensity. In some embodiments, the same data may be processed in parallel by both methods and the result of both analysis methods may be used to display or otherwise use a consensus of the two measurements or to check the validity of measurements obtained by one method against measurements obtained by the other method.

The average spectral power of the EMG data may be used to generate a quantitative or semi-quantitative measure of shivering intensity by, for example, recording one of the following values:

a. The amplitude of the peak spectral power within an appropriate frequency range that is typical for shivering EMG.

b. The area under the curve of the spectral power within an appropriate frequency range that is typical for shivering EMG.

c. Analysis of the appearance of different peaks corresponding to different frequencies of shivering that occur as shivering becomes more intense.

d. Analysis of the change of such spectral peaks or patterns as a function of time.

The shivering intensity thus measured may be used to generate a continuous variable or score variable as a function of time that represents shivering intensity. The shivering intensity scale or score may be displayed numerically or graphically for clinical use; or, the shivering intensity scale or score can be used as a means to influence other variables under control in related applications (such as the control of counterwarming in the methods according to embodiments of the invention).

The gain of the amplification of the ECG+EMG data described above will determine whether low amplitude shivering EMG is detected by the above process, and accordingly amplifier gain may be adjusted as follows:

a. Higher amplifier gain settings can be chosen by the user for applications in which the user wishes to detect more subtle degrees of shivering.

b. Amplifier gain settings may be pre-adjusted by the system or the user such that prior to application of therapeutic cooling (and thus prior to shivering), the baseline amplifier gain is increased until noise not related to shivering is detected and the gain is set to a level just below this point.

For the ECG+EMG data analysis system, the user may in some embodiments choose the best electrode pair(s) to be analyzed by electronic means by way of the operator interface to yield the optimal ECG morphology for analysis. In some embodiments, the shivering analysis system may automatically select the optimal electrode pair(s) for analysis based on computerized identification of specific ECG components, for example by selecting the electrode pair with the highest R wave amplitude.

In some embodiments of the direct motion-sensing shivering detection system, an accelerometer or other vibration sensor capable of measuring movement in three dimensions is used. In these embodiments, the data from each of the three planes (x, y, and z) are acquired in digital form from the device, and these data can be used in different ways. In some embodiments, the plane with the highest amplitude signal or highest spectral energy in a frequency range associated with shivering may be used for analysis. In other embodiments, the average signal from the three planes is used for analysis. In other embodiments, the vector of maximal shivering movement may be determined from the relative amplitude of the waveforms from each plane or from the relative spectral energy in a frequency range associated with shivering from each plane, and the shivering waveform for this vector of maximal shivering movement may be reconstructed by appropriate weighted averaging of the waveforms from the three planes for use in analysis of shivering. In other embodiments, the determination of the vector of maximal rhythmic movement is determined from the relative spectral energy in a frequency range associated with shivering from each plane and this value is tracked over time to discriminate between non-shivering muscle movements or activity (which have a changing vector of movement) and shivering activity (which has a relatively constant vector of movement for a given muscle group).

For detection based on direct sensing of periodic movement (vibration), wavelet analysis (spectral processing) such as fast Fourier transform (FFT) analysis may be carried out directly on the data signal from the sensor. Or in some instances preferably, an autocorrelation step may be carried out prior to performing the wavelet analysis. The peak of the resulting curve, or the area under the curve, or other approach as described for treatment of electrode-derived data, can be used to generate the shivering quantification signal. As in the treatment of electrode-derived data, the frequency range in the vibration-sensor derived data stream can optionally limited to a range appropriate for shivering. A "baseline" pre-shivering data stream can be obtained from the vibration-sensor data, as in the electrode data, to minimize (or at least reduce) contributions of mechanical vibrations not related to shivering. For example wavelet components related to movements or vibrations transmitted mechanically from devices in the treatment environment (for example the ICU) such as pumps or ventilators could be removed in this way. Non-periodic or less regular vibration contaminants such as patient movement, or coughing, or contact with other persons, can be minimized by averaging the vibration FFT over time and by use of an autocorrelation function prior to each FFT (thereby enhancing the analysis of rhythmic signals), so that non-periodic and non-continuous data are eliminated from the analysis.

Example 1

Figure 9A:
FIGS. 9A, 9B, 9C, 9D, 9E, 9F and 9G are plots of data, detected in a shivering subject using surface electrodes and analyzed according to an aspect of the invention.
Figure 9B:
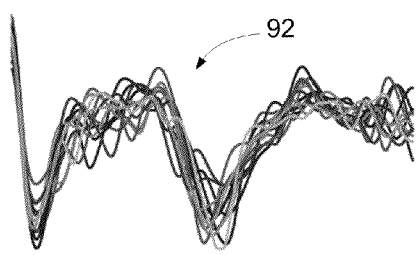
Figure 9C:
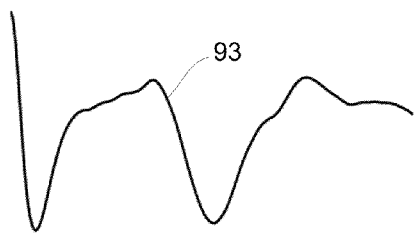
Figure 9D:
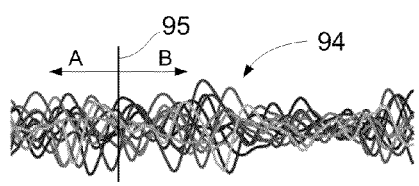
Figure 9E:
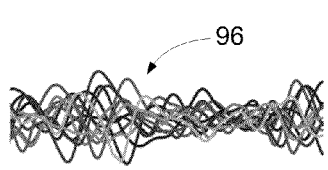
Figure 9F:
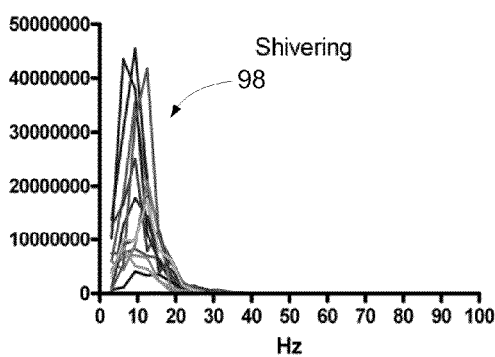
Figure 9G:
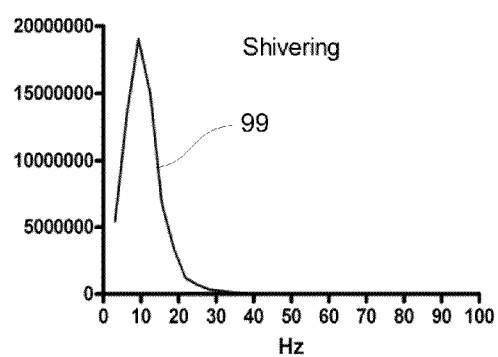

For detection based on electrode-based sensing of electrical activity, one or more electrodes may be placed on or in the body at sites susceptible to shivering. FIG. 9A is a plot (trace) of a data signal obtained over a duration of several seconds (the ECG epoch), by an ECG electrode applied to the skin of a shivering subject, at a site overlying a muscle mass (the pectoral muscles) that is susceptible to shivering. ECG cycles are clipped from the ECG epoch, and outlier QRS complexes are rejected. The resulting ECG cycles are aligned on the positive peak of the QRS complex of each, as shown at 92 in FIG. 9B. Then the aligned ECG cycles are averaged, yielding a result as shown at 93 in FIG. 9C. Then the data shown in FIG. 9C are subtracted from the data for each of the aligned ECG cycles shown in FIG. 9B, to yield a result as shown at 94 in FIG. 9D. The data of FIG. 9D are then clipped at 95, to remove the initial QRS portion of the traces (indicated by arrow A), and leaving the portion 96 as shown in FIG. 9E (corresponding to arrow B in FIG. 9D, for autocorrelation followed by fast Fourier transform (FFT). FIG. 9F shows the resulting power spectral density (PSD) curves derived from the data in the traces of FIG. 9E. The PSDs for the traces are then averaged to yield the average PSD curve as shown in FIG. 9G. The PSD curves (peaks) 98, 99 represent a quantification of shivering.

Figure 10A:
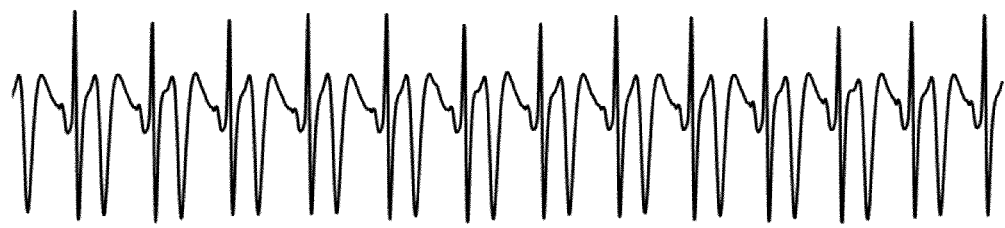
FIGS. 10A, 10B, 10C, 10D, 10E, 10F and 10G are plots of data, detected in a non-shivering subject using an electrode and analyzed according to an aspect of the invention.
Figure 10B:
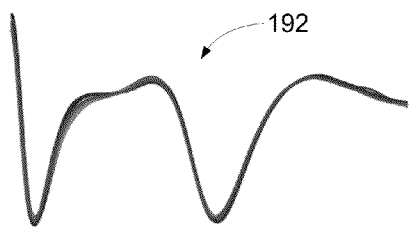
Figure 10C:
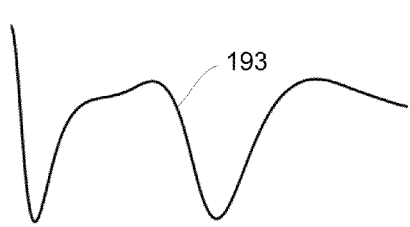
Figure 10D:
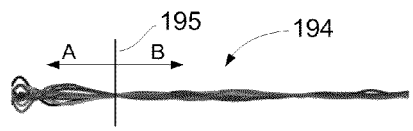
Figure 10E:
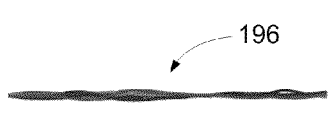
Figure 10F:
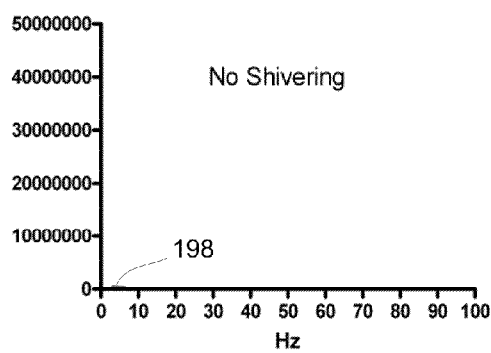
Figure 10G:
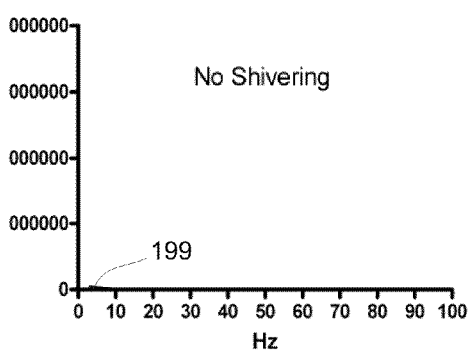

FIG. 10A is a plot (trace) of data obtained generally as described with reference to FIG. 9A from a subject who was not shivering; and FIGS. 10B-10G illustrate analysis of the data in a manner generally similar to that described with reference to FIGS. 9A-9G. The data in FIG. 10A were obtained over a duration of several seconds (the ECG epoch), by an ECG electrode applied to the skin of a subject who is not shivering, at a site overlying a muscle mass (the pectoral muscles) that is susceptible to shivering. ECG cycles are clipped from the ECG epoch, and the resulting ECG cycles are aligned on the positive peak of the QRS complex of each, as shown at 192 in FIG. 10B. Then the aligned ECG cycles are averaged, yielding a result as shown at 193 in FIG. 10C. Then the data shown in FIG. 10C are subtracted from the data for each of the aligned ECG cycles shown in FIG. 10B, to yield a result as shown at 194 in FIG. 10D. The data of FIG. 10D are then clipped at 195, to remove the initial QRS portion of the traces (indicated by arrow A), and leaving the portion 196 as shown in FIG. 10E, for autocorrelation followed by fast Fourier transform (FFT). FIG. 10F shows the resulting power spectral density (PSD) curves derived from the data in the traces of FIG. 10E. The PSDs for the traces are then averaged to yield the average PSD curve as shown in FIG. 10G. As the very low PSD curves (peaks) show at 198, 199, shivering has been substantially reduced.

Figure 12:
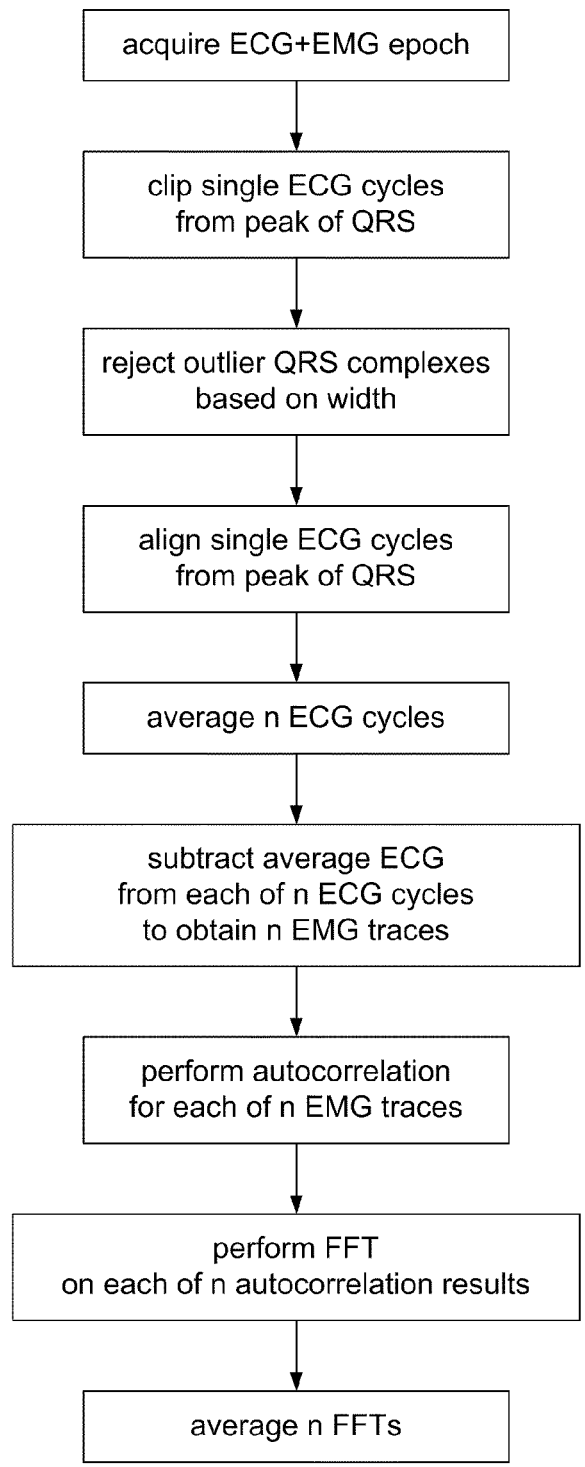
FIG. 12 is a flowchart showing stages in a shivering quantification process employing electrode detection according to an embodiment of the invention.

FIG. 12 is a flow chart illustrating stages in an example of a process for treatment of data acquired from electrode.

Example 2

Figure 11A:
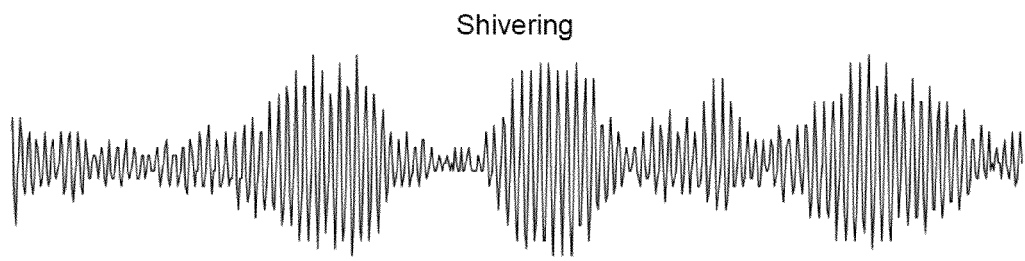
FIG. 11A shows a plot of data detected in a shivering subject using an accelerometer.
Figure 11B:
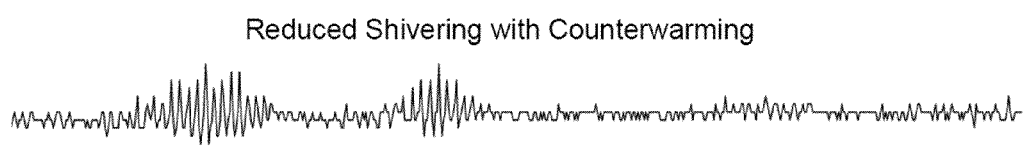
FIG. 11B shows a plot of data detected in a subject as in FIG. 11A, showing reduction of shivering by applied counterwarming.
Figure 11C:
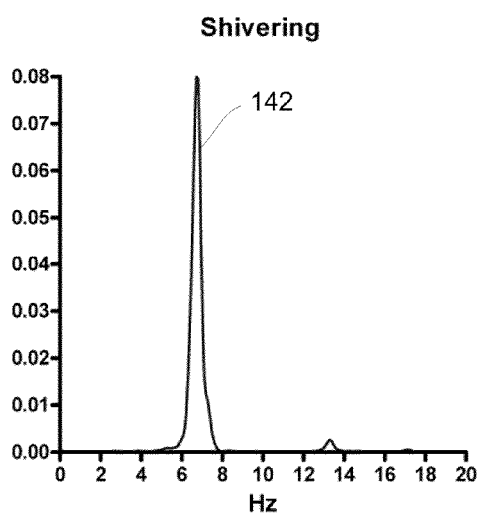
FIG. 11C shows the result of analysis of data as in FIG. 11A according to an embodiment of the invention.
Figure 11D:
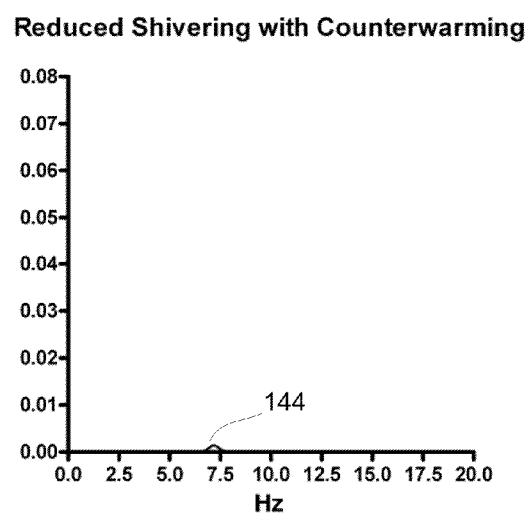
FIG. 11D shows the result of analysis of data as in FIG. 11B according to an embodiment of the invention.

For detection based on direct sensing of periodic movement (vibration), one or more motion sensors, such as an accelerometer, may be applied to any exposed skin region overlying a muscle group engaged in shivering. The sensors may be held in place using an adhesive such as a hydrogel, or by an elastic band. FIG. 11A is a plot (trace) of a data signal from an accelerometer held on the skin of a shivering subject, at a site overlying a muscle mass susceptible to shivering (the pectoral muscles). In this demonstration the data were obtained using an accelerometer. FIG. 11B is a plot (trace) of a data signal, obtained in the same manner, from the same subject following application of counterwarming. FIG. 11C is a plot showing the power spectral density curve derived from the data of FIG. 11A by autocorrelation followed by fast Fourier transform (FFT). A high narrow peak 142 at about 6.75 Hz, and a much lower peak appears at about 13.3 Hz. FIG. 11D is a plot showing the power spectral density (PSD) curve derived from the data of FIG. 11B similarly by autocorrelation followed by fast Fourier transform (FFT). Shivering has been substantially reduced; only a very low peak 144 at about 7.2 Hz remains.

Figure 13:
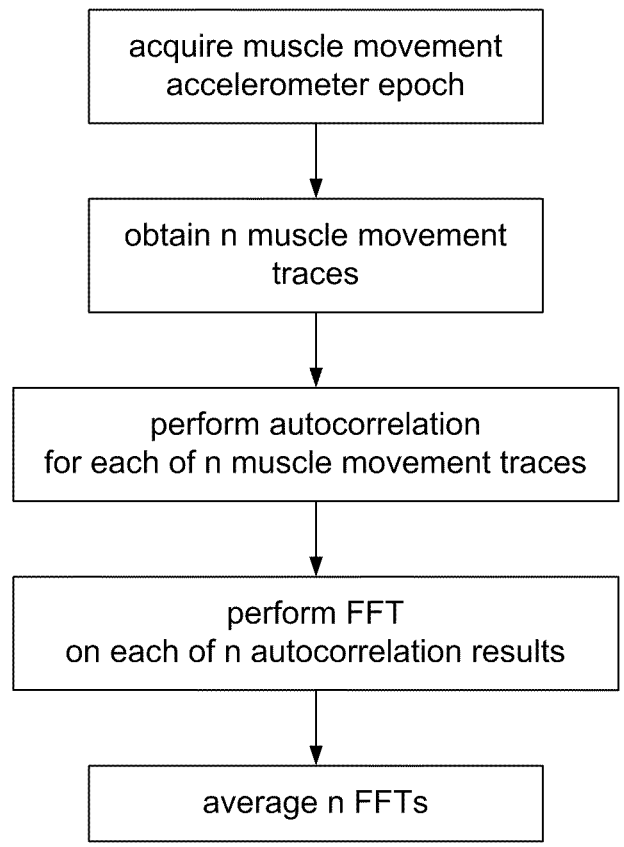
FIG. 13 is a flowchart showing stages in a shivering quantification process employing accelerometer detection according to an embodiment of the invention.

FIG. 13 is a flow chart illustrating stages in an example of a process for treatment of data acquired from an accelerometer.

Counterwarming according to the invention may be applied for the minimization, prevention, or treatment of shivering such that any of the following pertain.

1. The degree of counterwarming applied may be adjusted according to the amount of cooling being applied to the core at any given moment;
2. The degree of counterwarming applied may be adjusted according to the degree of shivering measured at a given moment (using for example the methods and apparatus described herein for the quantification/measurement of shivering);
3. The degree of counterwarming applied may adjusted according to the patient's body temperature as measured by standard methods;
4. The degree of counterwarming applied may be adjusted according to any combination of: cooling temperature, shivering intensity, and/or patient temperature with any of a variety of additional variables, constants, proportionality coefficients; or any other mathematical manipulations or interactions of these variables;
5. The degree of counterwarming applied may adjusted according to the rate of change of any of: change in cooling temperature per unit time, change in shivering intensity per unit time, and/or change in patient temperature per unit time; or any other mathematical manipulation or interaction of these variables (including but not limited to change in any variable per the square of the unit time);
6. The degree of counterwarming as influenced by any of the above methods may be accomplished in any of several different ways, including: changes in the temperature of warming applied to all treated body regions; changes in the temperature of warming applied to specific treated body regions; changes in the pattern of warming applied to selective treated body regions (warming applied to different body regions at different times according to any number of patterns); application of warming in a successive fashion to sequential body regions (e.g., to ears, then ears+hands, then ears+hands+feet); application of selective warming to smaller regions such as fingers or toes; or application of warming to different body regions such that a spatial pattern of shivering detected influences the spatial pattern of warming applied;
7. The application of warmth to various body regions includes any method for application of heat that can be controlled by the methods described herein, including but not limited to heated mittens, heated booties, heated ear muffs, or heated blankets above or below the body, and including but not limited to any conventional method for heat transfer such as warming with circulating water (or other liquid) or warming by insulated heating coils;
8. The areas treated with counterwarming may be any exposed body region not being used for cooling;
9. The intensity of warmth application to various body regions may be performed in various patterns with variation of intensity of warmth applied to different regions and may be used to create gradients of warmth;
10. The degree of counterwarming applied may be adjusted according to any number of computer learning algorithms to determine over time an optimal means of shivering treatment in an individual patient;

The methods in various embodiments can employ any of a variety of technical means of body cooling, warmth application, or measurement of shivering, including but not limited to the method for shivering quantification described above.

Quantification according to the invention of repetitive adventitial movements other than shivering can be very useful medically, including for example in the measurement and quantification of shaking, tremors, or convulsions. Such information could be particularly useful in tracking disease progression, or in tracking effects of medications or surgical interventions.

Quantification of the motor component of seizures can be particularly useful in seizure monitoring settings. Conventionally epilepsy patients are frequently admitted for monitoring using video EEG telemetry, in which the electrical component of the seizures is monitored by continuous EEG, but the convulsive movements are captured only by video. Seizure monitoring could be improved according to the invention, by placing motion detectors (such as accelerometers or ECG or EMG electrodes) in appropriate locations on the patient's body, and correlating the processed signals from motion detectors in real-time or near real-time with the electrographic seizure activity.

As may be appreciated, shivering may be quantified by processing signals obtained concurrently from electrodes and from repetitive movement (vibration) sensors, and associations between mechanical movement and electrical activity can be tracked.

In certain of the signal analysis approaches outlined above, particularly useful in detecting and measuring shivering in a subject, a combined signal including superimposed ECG and EMG components is treated by identifying and storing epochs based on a feature of the ECG component, averaging the stored combined signal epochs to obtain an average ECG signal substantially free of the EMG component, subtracting the average ECG signal from each of the stored combined signal epochs to obtain isolated EMG epochs, and thereafter further treating the EMG epochs to quantify shivering. At least some of the signal and data processing manipulations are carried out using a machine such as a microprocessor programmed to carry out the particular manipulations.

As may be appreciated, systems are more generally provided for isolating a signal of interest from a combined signal containing superimposed first and second signals, in certain circumstances. Particularly, where the first signal is the signal of interest, the first signal may have any of a variety of properties; the second signal must include recurring epochs or cycles of a stereotyped waveform, and may in addition have a relationship to an external event, such as an external trigger. Examples of such signals include, but are not limited to, the recurring electrical waveform of an electrocardiogram, a repetitive sound waveform, or a repetitive mechanical vibration.

The process, generally, is as follows.

The combined signal (signal A+signal B) is digitally sampled using a standard analog-to-digital converter at a sample rate sufficient to capture relevant details of signal A and of signal B. Epochs of the combined signal (A+B) are then stored in buffers. The initial sample of each epoch is determined by signal processing to identify one or more characteristic features of the repetitive signal B. For example, if signal B has a notable peak, thresholding may be used to identify the peak in order to utilize the apex of the peak to index the initial sample of each epoch. Any feature of the repetitive and stereotyped signal B that may be identified by standard signal processing methods known in the art may be used to trigger the start of each stored epoch. For example the peak apex itself may be taken as the initial sample of an epoch; or, the peak may be identified by detecting its apex and some other feature of the peak (or some other feature of the repetitive signal) may be taken as the initial sample of the epoch. In specific applications in which signal B also has a temporal relationship to an external event, such as an external trigger, the external event may be used to select the start of each epoch, based on the temporal relationship between the external event and signal B. Typically, each epoch will last until the sample immediately prior to the first sample of the next epoch, but shorter epoch durations may be preferable in certain applications. Once a certain number of combined signal (A+B) epochs are stored in buffers, the signals in the buffers are averaged. A sufficient number of epochs are averaged in order to obtain an average signal B free of signal A, according to an established method of signal averaging for noise reduction known in the art, and the results are stored in a new buffer. In order to obtain epochs of signal A having minimal contamination by signal B, the average Signal B is then subtracted away from each stored combined signal (A+B) epoch, with the result of each subtraction stored in a new buffer. The stored isolated signal A epochs may then be subjected to desired signal analysis. If the epochs were selected such that each epoch extended until the sample immediately prior to the first sample of the following epoch, the signals may be rejoined end to end to reconstruct the longer recording of signal A, if desired.

Combined signals of any of a variety of types, from any of a variety of sources, may be treated in this manner.

Other embodiments are within the claims.

I claim:

1. A method for quantifying shivering in a subject, comprising obtaining a signal from a muscle mass that is susceptible to shivering, the signal including an ECG component and an EMG component, and quantifying shivering by analysis of the signal by a microprocessor.

2. The method of claim 1, further comprising displaying a measure of an intensity of the quantified shivering.

3. A method for quantifying shivering in a subject, comprising obtaining a signal from a muscle mass that is susceptible to shivering; and quantifying shivering by analysis of the signal using an autocorrelation followed by a Fourier analysis by a microprocessor.

4. The method of claim 3, further comprising displaying a measure of an intensity of the quantified shivering.

5. The method of claim 3 wherein obtaining the signal comprises detecting movement using a motion detector.

6. The method of claim 3 wherein obtaining the signal comprises detecting movement using an accelerometer.

7. The method of claim 1 wherein obtaining the signal comprises obtaining an electrical signal from one or more electrodes.

8. The method of claim 7 wherein obtaining the signal comprises obtaining an EMG signal.

9. The method of claim 7 wherein obtaining the signal comprises obtaining a combined ECG and EMG signal.

10. The method of claim 1 wherein obtaining the signal comprises directly detecting vibration of the muscle mass and detecting an electric signal from the muscle mass.

11. A method for quantifying shivering in a subject, comprising detecting a combined ECG and EMG signal from a muscle mass that is susceptible to shivering and processing the signal to remove the ECG component; and quantifying shivering by analysis of the processed signal by a microprocessor.

12. The method of claim 11 wherein detecting the combined ECG and EMG signal comprises detecting a signal from one or more electrodes at one or more sites overlying the muscle mass.

13. The method of claim 11 wherein detecting a combined ECG and EMG signal comprises detecting a signal from one or more electrodes at one or more sites.

14. The method of claim 11, further comprising digitizing the combined ECG and EMG signal, and performing a wave analysis on the digitized combined signal.

15. The method of claim 14 wherein performing a wave analysis comprises performing a spectral density analysis on the combined signal.

16. The method of claim 14 wherein performing a wave analysis comprises carrying out a wave analysis on a frequency range of a spectrum that corresponds to a shivering EMG.

17. The method of claim 11 wherein processing the signal comprises digitizing the combined signal, segmenting the digitized combined signal to a set of traces, each said trace comprising at least a portion of a cardiac cycle, signal averaging the digitized traces to provide ECG data having a reduced contribution of EMG data, and subtracting the averaged ECG data from the combined EMG and ECG data to yield shivering EMG traces having a reduced contribution of ECG data.

18. The method of claim 17, comprising aligning the traces based on a feature of the ECG waveform.

19. The method of claim 18, comprising aligning the traces based on a peak of a QRS complex of the ECG.

20. The method of claim 18, comprising signal averaging a selected segment of the traces, the selected segment including regions having minimal ECG data elements.

21. The method of claim 11, further comprising detecting atypical ECG morphologies and removing traces containing atypical ECG morphologies from further analysis.

22. The method of claim 14 wherein performing the wave analysis comprises carrying out an averaged FFT analysis.

23. The method of claim 22 wherein carrying out the averaged FFT analysis comprises performing a FFT on each shivering EMG tracing, and averaging a resulting FFT spectra to yield an averaged FFT spectrum.

24. The method of claim 17, further comprising performing an autocorrelation function on each shivering EMG trace, and performing a wave analysis on results of the autocorrelation.

25. The method of claim 24 wherein performing a wave analysis comprises performing a Fourier analysis.

26. The method of claim 14 wherein quantifying shivering comprises determining an amplitude of a peak spectral power within a frequency range for shivering EMG.

27. The method of claim 14 wherein quantifying shivering comprises determining the area under the curve of the spectral power within a frequency range that is typical for shivering EMG.

28. The method of claim 14 wherein quantifying shivering comprises analyzing appearances of different peaks corresponding to different frequencies of shivering that occur as shivering becomes more intense.

29. The method of claim 14 wherein quantifying shivering comprises analyzing change of spectral peaks or patterns as a function of time.

30. A method for quantifying shivering in a subject, comprising: at a time when the subject would not be expected to shiver, obtaining a first signal from a muscle mass that is susceptible to shivering, and processing the baseline signal by spectral analysis by a microprocessor; at a time when the subject may be expected to shiver, obtaining a second signal, and processing the second signal by spectral analysis by a microprocessor; and subtracting results of one spectral analysis from results of the other spectral analysis to obtain a spectrum that represents only a shivering component.

31. Apparatus for quantifying shivering in a subject, comprising means for obtaining a signal from a muscle mass that is susceptible to shivering, the signal including an ECG component and an EMG component, and means for analyzing the signal.

32. Apparatus for quantifying shivering in a subject, comprising means for obtaining a signal from a muscle mass that is susceptible to shivering; and means for analyzing the signal using an autocorrelation followed by a Fourier analysis.

33. The apparatus of claim 32 wherein the means for obtaining a signal comprises a direct motion detector and electrical or wireless operative connection between the detector and a signal processor.

34. The apparatus of claim 33 wherein the direct motion detector comprises an accelerometer.

35. The apparatus of claim 32 wherein the means for obtaining a signal comprises an indirect motion detector and electrical or wireless operative connection between the detector and a signal processor.

36. The apparatus of claim 31 wherein the indirect motion detector comprises one or more electrodes adapted for placement in or on a surface of the body of the patient.

37. The apparatus of claim 36 wherein the indirect motion detector comprises one or more ECG electrodes.

38. The apparatus of claim 36 wherein the indirect motion detector comprises one or more EMG electrodes.

39. The apparatus of claim 31 wherein the means for analyzing the signal comprises a signal processor adapted to receive signals from the means for obtaining the signal from the muscle mass.

40. The apparatus of claim 32 wherein the means for analyzing the signal comprises a signal processor adapted to receive signals from the means for obtaining the signal from the muscle mass.

* * * * *